(12) United States Patent
Gilotra et al.

(10) Patent No.: US 12,582,532 B2
(45) Date of Patent: Mar. 24, 2026

(54) DUAL MOBILITY CUP REVERSE SHOULDER PROSTHESIS

(71) Applicants: UNIVERSITY OF MARYLAND, COLLEGE PARK, College Park, MD (US); UNIVERSITY OF MARYLAND, BALTIMORE, Baltimore, MD (US); THE UNITED STATES GOVERNMENT AS REPRESENTED BY THE DEPARTMENT OF VETERANS AFFAIRS, Washington, DC (US)

(72) Inventors: Mohit Gilotra, Ellicott City, MD (US); Rayan Khalid Alabsi, Rockville, MD (US); Tejasvi Subramanya, Oxnard, CA (US)

(73) Assignees: University of Maryland, College Park, College Park, MD (US); University of Maryland, Baltimore, Baltimore (MD); The United States Government as Represented by the Department of Veterans Affairs, Washington, DC (US)

( * ) Notice: Subject to any disclaimer, the term of this patent is extended or adjusted under 35 U.S.C. 154(b) by 700 days.

(21) Appl. No.: 17/794,215

(22) PCT Filed: Jan. 21, 2021

(86) PCT No.: PCT/US2021/014396
§ 371 (c)(1),
(2) Date: Jul. 20, 2022

(87) PCT Pub. No.: WO2021/150740
PCT Pub. Date: Jul. 29, 2021

(65) Prior Publication Data
US 2023/0137504 A1 May 4, 2023

Related U.S. Application Data

(60) Provisional application No. 62/963,752, filed on Jan. 21, 2020.

(51) Int. Cl.
*A61F 2/40* (2006.01)
*A61F 2/30* (2006.01)

(52) U.S. Cl.
CPC .......... *A61F 2/4081* (2013.01); *A61F 2/4014* (2013.01); *A61F 2/4059* (2013.01);
(Continued)

(58) Field of Classification Search
CPC .... A61F 2/4081; A61F 2/4014; A61F 2/4059; A61F 2002/30367; A61F 2002/4085;
(Continued)

(56) References Cited

U.S. PATENT DOCUMENTS 3,916,451 A 11/1975 Buechel et al.
4,206,517 A 6/1980 Pappas et al.
(Continued)

FOREIGN PATENT DOCUMENTS

EP 1649836 A2 4/2006
GB 2166654 A 5/1986
(Continued)

OTHER PUBLICATIONS

PCT International Search Report and Written Opinion, PCT/US2021/014396, Apr. 8, 2021, 8 pages.
(Continued)

*Primary Examiner* — Yashita Sharma
(74) *Attorney, Agent, or Firm* — Quarles & Brady LLP; Yakov S. Sidorin; Victoria C. Cook

(57) ABSTRACT

A reverse shoulder prosthesis system is provided. The system can include a the convex surface of the glenosphere and the concave surface of the humeral socket. The convex
(Continued)

surface, a humeral socket can have a concave surface, and a cup is positioned between cup can be moveable relative to the glenosphere and to the humeral socket.

23 Claims, 15 Drawing Sheets

(52) U.S. Cl.
  CPC .............. *A61F 2002/30367* (2013.01); *A61F 2002/4085* (2013.01)

(58) Field of Classification Search
  CPC .......... A61F 2/4612; A61F 2002/30245; A61F 2002/30345; A61F 2002/30354; A61F 2002/30574; A61F 2002/30604; A61F 2002/30662; A61F 2002/30663; A61F 2002/30784; A61F 2002/30827; A61F 2002/30934; A61F 2002/4018; A61F 2002/4022; A61F 2002/4037; A61F 2002/4062; A61F 2002/4681; A61F 2/40; A61F 2/34; A61F 2/36
  See application file for complete search history.

(56) References Cited

U.S. PATENT DOCUMENTS

| | | | |
|---|---|---|---|
| 6,790,234 | B1 | 9/2004 | Frankle |
| 8,771,367 | B2 | 7/2014 | Armacost et al. |
| 8,945,229 | B2 | 2/2015 | Lappin |
| 9,445,903 | B2 | 9/2016 | Meridew et al. |
| 9,763,799 | B2 | 9/2017 | Smits et al. |
| 2011/0060417 | A1 | 3/2011 | Simmen et al. |
| 2013/0150975 | A1 | 6/2013 | Iannotti et al. |
| 2014/0303743 | A1 | 10/2014 | Choudhury et al. |
| 2019/0021867 | A1 | 1/2019 | Lawrence et al. |

FOREIGN PATENT DOCUMENTS

| | | |
|---|---|---|
| WO | 2015/134626 A2 | 9/2015 |
| WO | 2017/125750 A1 | 7/2017 |

OTHER PUBLICATIONS

European Patent Office, Extended Search Report, Application No. 21744761.4, Dec. 14, 2023, 10 pages.
Ackland et al., Muscle and Joint Function After Anatomic and Reverse Total Shoulder Arthroplasty Using a Modular Shoulder Prosthesis, Journal of Orthopaedic Research, 2019, 37:1988-2003.
ASTM International, Designation: F1378-18, Standard Specification for Shoulder Prostheses, 2019, 6 pages.
Barco et al., Complications in Reverse Shoulder Arthroplasty, EFORT Open Reviews, 2016, 1:72-80.
Berhouet et al., Influence of Glenoid Component Design and Humeral Component Retroversion on Internal and External Rotation in Reverse Shoulder Arthroplasty: A Cadaver Study, Orthopaedics & Traumatology: Surgery & Research, 2013, 99(8):887-894.
Biomet, Active Articulation(TM) E1(R) Dual Mobility Hip System, https://web.archive.org/web/20140325052042/http://www.biomet.com/web_accents/biomet_products/activearticulation.cfm, 2014, 3 pages.
Biomet (Zimmer Biomet), Active Articulation E1 Dual Mobility Hip System, https://www.zbmarketsmart.com/zimmer/iframe_active_articulation/, accessed Apr. 14, 2023, 2 pages.
Boileau et al., Revision Surgery of Reverse Shoulder Arthroplasty, Journal of Shoulder and Elbow Surgery, 2013, 22(10):1359-1370.
Chalmers et al., Expanding Roles for Reverse Shoulder Arthroplasty, Current Reviews in Musculoskeletal Medicine, 2016, 9:40-48.
Erickson et al., A Comprehensive Evaluation of the Association of Radiographic Measures of Lateralization on Clinical Outcomes Following Reverse Total Shoulder Arthroplasty, Journal of Shoulder and Elbow Surgery, 2022, 31(5):963-970.
Familiari et al., Reverse Total Shoulder Arthroplasty, EFORT Open Reviews, 2018, 3:58-69.
Gutierrez et al., Hierarchy of Stability Factors in Reverse Shoulder Arthroplasty, Clinical Orthopaedics and Related Research, 2008, 466:670-676.
Gutierrez, The Biomechanics of Reverse Shoulder Arthroplasty, USF Tampa Graduate Theses and Dissertations, 2009, 146 pages.
Halder et al., Anatomy and Biomechanics of the Shoulder, Orthopedic Clinics, 2000, 31(2):159-176.
Kim et al., Difficulty in Performing Activities of Daily Living Associated with Internal Rotation After Reverse Total Shoulder Arthroplasty, Journal of Shoulder and Elbow Surgery, 2020, 29(1):86-94.
Kohut et al., Inverted-Bearing Reverse Total Shoulder Arthroplasty: Scapular Notching Does Not Affect Clinical Outcomes and Complications at up to 7 Years of Follow-Up, Journal of Shoulder and Elbow Surgery, 2022, 31(4):868-874.
Kozak et al., An Update on Reverse Total Shoulder Arthroplasty: Current Indications, New Designs, Same Old Problems, EFORT Open Reviews, 2021, 6:189-201.
Langlais et al., Dual Mobility Cemented Cups have Low Dislocation Rates in THA Revisions, Clinical Orthopaedics and Related Research, 2008, 466:389-395.
Langohr et al., The Effect of Glenosphere Diameter in Reverse Shoulder Arthroplasty on Muscle Force, Joint Load, and Range of Motion, Journal of Shoulder and Elbow Surgery, 2015, 24(6):972-979.
Patel et al., Trending a Decade of Proximal Humerus Fracture Management in Older Adults, JSES International, 2022, 6(1):137-143.
Rohman et al., Factors Associated with Improvement or Loss of Internal Rotation After Reverse Shoulder Arthroplasty, Journal of Shoulder and Elbow Surgery, 2022, 31(7):e346-e358.
Simovitch et al., Quantifying Success After Total Shoulder Arthroplasty: The Minimal Clinically Important Difference, Journal of Shoulder and Elbow Surgery, 2018, 27(2):298-305.
Simovitch et al., Impact of Scapular Notching on Reverse Total Shoulder Arthroplasty Midterm Outcomes: 5-year Minimum Follow-Up, Journal of Shoulder and Elbow Surgery, 2019, 28(12):2301-2307.
Smith&Nephew, Polarcup—Dual Mobility Hip System, https://web.archive.org/web/20190704023615/http://www.smith-nephew.com:80/professional/products/all-products/polarcup/, 2019, 5 pages.
Terrier et al., Activities of Daily Living with Reverse Prostheses: Importance of Scapular Compensation for Functional Mobility of the Shoulder, Journal of Shoulder and Elbow Surgery, 2013, 22(7):948-953.
Triplet et al., Functional Internal Rotation After Shoulder Arthroplasty: A Comparison of Anatomic and Reverse Shoulder Arthroplasty, Journal of Shoulder and Elbow Surgery, 2015, 24(6):867-874.
U.S. Food & Drug Administration, The 510(k) Program: Evaluating Substantial Equivalence in Premarket Notifications [510(k)], Jul. 28, 2014, 42 pages.
U.S. Food & Drug Administration, CFR—Code of Federal Regulations, Title 21, vol. 8, Sec. 888.3660 Shoulder Joint Metal/Polymer Semi-Constrained Cemented Prosthesis, Updated: Jan. 17, 2023, 3 pages.
U.S. Food & Drug Administration, 510(k) Premarket Notification, K172351, Device Name: AltiVate Reverse Humeral Stem, AltiVate Reverse Small Spacer, Altivate Reverse, Small Hemi-Adapter, AltiVate Reverse, Small Socket Insert, Last Updated: Apr. 10, 2023, 3 pages.
U.S. Food & Drug Administration, Product Classification, Shoulder Prosthesis, Reverse Configuration, Last Updated: Apr. 10, 2023, 3 pages.
University of Maryland, MPowering the State Fellows Develop Novel Shoulder Implant, https://fischellinstitute.umd.edu/news/story/mpowering-the-state-fellows-develop-novel-shoulder-implant, Oct. 1, 2019, 2 pages.
Verified Market Research, Global Shoulder Replacement Market Size by Procedure (Reverse Total Shoulder Replacement, Resur-

(56) References Cited

OTHER PUBLICATIONS facing Hemi Arthroplasty), By End-User (Orthopaedic Centers, Hospitals), By Geographic Scope and Forecast, Report ID: 10368, Published Apr. 2023, 9 pages.

Werner et al., Glenoid Lateralization Influences Active Internal Rotation After Reverse Shoulder Arthroplasty, Journal of Shoulder and Elbow Surgery, 2021, 30(11):2498-2505.

Woolf et al., Burden of Major Musculoskeletal Conditions, Bulletin of the World Health Organization, 2003, 81(9):646-656.

DUAL MOBILITY CUP REVERSE SHOULDER PROSTHESIS

CROSS-REFERENCE TO RELATED APPLICATIONS

This application claims priority to U.S. Patent Application No. 62/963,752 filed Jan. 21, 2020, and entitled, "Dual-Cup, Reverse Configuration Shoulder Prosthesis," which is hereby incorporated by reference in its entirety.

BACKGROUND

Musculoskeletal disorders including osteoarthritis, rheumatoid arthritis, rotator cuff tears, and traumatic fractures can be debilitating for patients and their families. The impaired functioning of these systems can be a burden for these patients (e.g., causing pain or creating an inability to successfully complete tasks). In fact, musculoskeletal complaints are a major cause of work-related absence in developed countries. With an aging population and increases in lifestyle factors (e.g., increased obesity and lack of physical activity), musculoskeletal disorders are expected to increase drastically.

Shoulder implants are prostheses implanted to alleviate problems associated with shoulder joints, such as pain due to arthritis or other anatomical malformations. Typical total shoulder implants replace the natural glenohumeral interface of the shoulder with an artificial ball and socket joint. For example, a standard anatomical total shoulder arthroplasty involves replacing a patient's glenoid with a concave plastic component and the patient's humeral head with a convex metal component. Because typical total shoulder replacements rely heavily on properly functioning rotator cuff muscles, this type of implant does not work well (and is likely to fail) in individuals with severely weak or damaged rotator cuff muscles.

As an alternative to the typical total shoulder replacement, the reverse total shoulder arthroplasty ("RTSA") was developed, which can work well (and minimize failure) in individuals with weak or damaged rotator cuff muscles. In a typical RTSA procedure, the natural glenohumeral interface is removed and is replaced with a convex part on the glenoid side of the shoulder, and concave part on the humeral side of the joint. Although more typical candidates for RTSA are those with cuff tear arthropathy, RTSA has been continually expanded to address various other conditions including severe proximal humeral fractures, glenoid and humeral bone loss, tumors, and failed shoulder arthroplasty (e.g., typically caused by dysfunction of rotator cuff muscles). Thus, the number of patients undergoing RTSA is only expected to increase over the years. For example, in 2011, about 21,692 people underwent reverse total shoulder arthroplasty in just the United States alone.

While RTSA procedures have generally been helpful for patients, they can be worse than typical total shoulder implants in some cases. Thus, it would be desirable to have improved systems and methods for reverse total shoulder prostheses.

SUMMARY OF THE DISCLOSURE

Some embodiments of the disclosure provide a reverse shoulder prosthesis system. The system can include a glenosphere configured to be securable to a scapula of a patient, the glenosphere can have a convex surface, a humeral socket having a concave surface, and a cup positioned between the convex surface of the glenosphere and the concave surface of the humeral socket. The cup can be moveable relative to the glenosphere and to the humeral socket.

In some embodiments, the system can include a humeral stem coupled to the humeral socket. The humeral stem can be configured to be secured to and within a humerus of the patient.

In some embodiments, the humeral socket is configured to be coupled to a humeral stem of a shoulder prosthesis system that has failed.

In some embodiments, the cup has a second concave surface and a second convex surface. The second concave surface of the cup and the convex surface of the glenosphere are configured to contact each other to define a first bearing surface as the cup moves relative to the glenosphere. The second convex surface of the cup and the concave surface of the humeral socket are configured to contact each other to define a second bearing surface as the humeral socket moves relative to the cup.

In some embodiments, the second concave surface of the cup has a first radius of curvature, and the second convex surface of the cup has a second radius of curvature. The first radius of curvature of the second concave surface can be smaller than the second radius of curvature of the second convex surface.

In some embodiments, the cup has a flange that extends circumferentially around a peripheral edge of the cup. The flange can extend radially away from a central axis of the cup.

In some embodiments, the humeral socket is configured to rotate relative to the cup in a first rotational direction until the humeral socket reaches the flange of the cup.

In some embodiments, a gap is defined between a surface of the flange and an edge of the humeral socket. In some embodiments, as the humeral socket rotates in a first rotational direction, the gap is minimized until the edge of the humeral socket contacts the surface of the flange.

In some embodiments, the flange is configured to prevent an edge of the humeral socket from rotating past an edge of the cup.

In some embodiments, when the edge of the humeral socket contacts the surface of the flange, the humeral socket and the flange are configured to prevent the humeral socket from moving further in the first rotational direction relative to the cup.

In some embodiments, the cup is configured such that when the edge of the humeral socket contacts the surface of the flange further rotation of the humeral socket in the first rotational direction causes the cup to rotate in the first rotational direction relative to the glenosphere.

In some embodiments, the flange includes an exterior concave surface that extends circumferentially around the cup. The concave surface of the humeral socket can have an arcuate lip that extends circumferentially around the humeral socket. The arcuate lip of the humeral socket can be configured to engage the exterior concave surface so that an outer surface of the flange is flush and aligned with an outer surface of the humeral socket.

In some embodiments, the system can include a baseplate coupled to the glenosphere. The flange of the cup is configured to prevent a peripheral edge of the humeral socket from contacting the baseplate. The flange of the cup is configured to prevent the peripheral edge of the humeral socket from contacting the glenosphere.

In some embodiments, the flange of the cup is configured to prevent the peripheral edge of the humeral socket from extending beyond the baseplate.

In some embodiments, the humeral socket is configured to rotate together with the cup, and is configured to rotate relative to the cup.

In some embodiments, the system can include a baseplate coupled to the glenosphere. The glenosphere can define a spherical portion that has a geometric center defined at an equator of the spherical portion. A distance between a coupling surface of the baseplate and the geometric center of the spherical portion can be a percentage of a radius of the glenosphere. The percentage can be between 20% and 70%

In some embodiments, the system can include a humeral stem coupled to the humeral socket. The humeral stem configured to be receivable within the humerus of the patient. A range of motion of the system can be greater than 60 degrees. The range of motion can be defined between a neutral position of the humeral stem relative to the glenosphere and a maximum rotational position of the humeral stem relative to the glenosphere. In the maximum rotational position, the cup can contact a baseplate or the end of the glenosphere.

In some embodiments, in the maximum rotational position a flange of the cup contacts the baseplate or the end of the glenosphere.

In some embodiments, the cup has opposing surfaces that are non-concentric. A thickness of the cup defined between the opposing surfaces varies based on an offset between the opposing surfaces.

In some embodiments, the system can include a baseplate coupled to the glenosphere. The cup can be configured to rotate relative to the glenosphere until the cup contacts the baseplate.

In some embodiments, the glenosphere can include a stem positioned at an end of the glenosphere, and a bore directed through the stem. The system can include a baseplate configured to be secured to a scapula of a patient. The baseplate can be sized to nest within the bore of the glenosphere, and the baseplate can be configured to be coupled to the glenosphere.

In some embodiments, the stem is integrally formed with the glenosphere.

Some embodiments of the disclosure provide a reverse shoulder prosthesis system. The system can include a glenosphere configured to be securable to a scapula of a patient, the glenosphere having a convex surface, a humeral socket having a concave surface, and a cup positioned between the convex surface of the glenosphere and the concave surface of the humeral socket. The cup can be snap-fitted onto the glenosphere.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the disclosure.

BRIEF DESCRIPTION OF THE DRAWINGS

The following drawings are provided to help illustrate various features of non-limiting examples of the disclosure, and are not intended to limit the scope of the disclosure or exclude alternative implementations.

DETAILED DESCRIPTION OF THE PRESENT DISCLOSURE

While RTSA procedures can reduce pain and provide relief, complication rates still remain undesirably high. For example, some sources of failure include the failure of the glenosphere (or the baseplate), infection, and dislocation of the humeral socket. However, even in patients without complications, typical RTSA procedures (and corresponding implants) can still present issues. For example, the functional range of motion of typical RTSA implants is significantly less than the functional range of motion of a typical shoulder joint—including a significantly limited internal rotation relative to the axial axis of the patient.

Some embodiments of the disclosure provide advantages to these issues (and others) by providing improved systems and methods for reverse total shoulder prostheses. In particular, some embodiments of the disclosure provide a reverse total shoulder implant that can include a glenosphere, a humeral socket, and a dual mobility cup located between the glenosphere and the humeral socket. The dual mobility cup provides advantages over conventional reverse total shoulder implants that include a glenosphere, a stationary liner, and a humeral socket. For example, in a conventional case, in order to increase the range of motion of the implant, the glenosphere is increased in size (radius) and/or center of rotation thereby increasing the articulating surface of the implant. However, by increasing the radius of the glenosphere and/or the center of rotation offset, there is an, increase in undesirable forces on the implant (e.g., increasing torque on the baseplate).

Because the dual mobility cup can advantageously articulate with both the glenosphere and the humeral socket, the range of motion for the implant is increased. In other words, the movement of the dual mobility cup with a surface of the glenosphere provides one range of motion for the implant, and the movement of the dual mobility cup with a surface of the humeral socket provides a second range of motion for the implant. These ranges of motion collectively provide an increased range of motion for the implant, which is larger (and more dynamic) than the conventional reverse total shoulder implants. Additionally, to provide a reasonable range of motion, the glenosphere of the conventional reverse total shoulder implant must be larger than the glenosphere of the reverse total shoulder implant of this disclosure. Thus, the smaller glenosphere of the reverse total shoulder implant of this disclosure allows for decreased undesirable stresses on the implant (e.g., a decrease in torque on the implant due to a decrease in the offset between the center of rotation of the glenosphere and the mounting location of the glenosphere).

Figure 1:
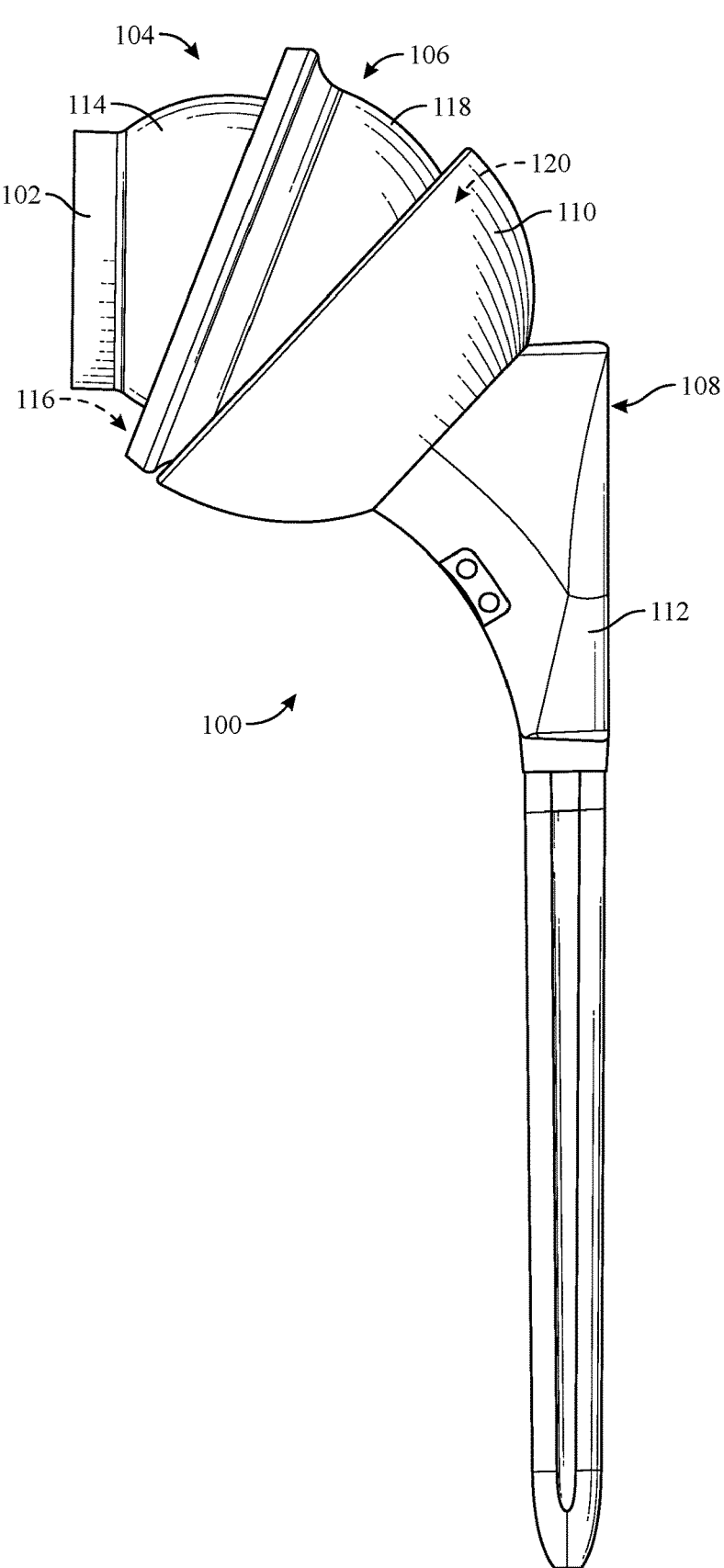
FIG. 1 is a side view of a reverse shoulder prosthesis system in an assembled configuration.

FIG. 1 shows a side view of a reverse shoulder prosthesis system 100 for a reverse total shoulder replacement in an assembled configuration. The system 100 can include a baseplate 102, a glenosphere 104 coupled to the baseplate 102, a cup 106, and a humeral component 108 having a socket 110 and a stem 112. As shown, one end of the baseplate 102 is coupled to the glenosphere 104, while an opposing end of the baseplate 102 can be coupled to a bone of a patient (e.g., the glenoid fossa of the scapula). In some cases, the baseplate 102 can be coupled to the bone using fasteners (e.g., screws, bolts, etc.), adhesives (e.g., cements), etc. For example, the fasteners can be inserted through the baseplate 102 and into the bone to mount the baseplate 102 to the bone of the patient.

The glenosphere 104 can be coupled to the baseplate 102 in various ways. For example, the glenosphere 104 can be coupled via an adhesive (e.g., cemented) to the baseplate 102, can be coupled via fasteners to the baseplate 102, or can be snap-fitted over the baseplate 102 (e.g., when an interior diameter of the glenosphere 104 has a larger diameter than the diameter of the baseplate 102). In some embodiments, the baseplate 102 can be nested entirely (or partially) within the glenosphere 104 so that the glenosphere 104 encapsulates the baseplate 102. In other configurations, the baseplate 102 can be exteriorly located relative to the glenosphere 104. In some embodiments, the baseplate 102 and the glenosphere 104 can both be formed of a metal (e.g., Titanium alloy, Cobalt Chromium alloy, etc.).

In some embodiments, the baseplate 102 and the glenosphere 104 can each include threads so that the glenosphere 104 can be threadingly engaged with the baseplate 102 to couple the glenosphere 104 to the baseplate 102. For example, in some cases, the peripheral surface of the baseplate 102 can include threads and an interior surface of the glenosphere 104 can include threads. In this way, after the baseplate 102 is secured to the bone of the patient, the glenosphere 104 can be rotated to threadingly engage the baseplate 102 to secure the glenosphere 104 to the baseplate 102. In some embodiments, the glenosphere 104 can be coupled to the baseplate 102 via a tapered engagement. For example, a taper (e.g., a Morse taper) of the glenosphere 104 and a taper (e.g., a Morse taper) of the baseplate 102 can be engaged together to couple the glenosphere 104 to the baseplate 102.

The glenosphere 104 defines a spherical portion having an exterior surface 114 that is convex, which can interface and articulate with the cup 106. The spherical portion of the glenosphere 104 also has a geometric center that is defined at the equator of the spherical portion. The distance from this geometric center and a surface of the bone that the baseplate 102 is coupled to (or the vertical surface of the baseplate 102 as shown in the view of FIG. 1) defines a total offset of the glenosphere 104. As described above, decreasing this offset can be desirable in that the torque and other forces provided to the baseplate 102 is also decreased, which can increase the longevity of the implant and decrease the likelihood of implant failure.

As illustrated, the cup 106 is positioned between the glenosphere 104 and the socket 110 of the humeral component 108, and is configured to move relative to the glenosphere 104 and relative to the socket 110. For example, the cup 106 has opposing surfaces 116, 118, having opposing concavities. In particular, the surface 116 of the cup 106 is concave, while the surface 118 of the cup 106 is convex. The surface 116 of the cup 106 is an interior surface of the cup 106 that engages with the exterior surface 114 of the glenosphere 104 to provide a bearing surface in which the surface 116 of the cup 106 slides along the exterior surface 114 of the glenosphere 104. In other words, the surface 116 of the cup 106 articulates with and relative to the exterior surface 114 of the glenosphere 104. The surface 118 of the cup 106 is an exterior surface of the cup 106 that engages with an inner surface 120 of the socket 110 (e.g., which is concave) to provide a bearing surface in which the surface 118 of the cup 106 slides along the surface 120 of the socket 110 (or the surface 120 of the socket 110 slides along the surface 118). In other words, the surface 118 of the cup 106 articulates with and relative to the surface 120 of the socket 110.

In some embodiments, the materials of the reverse shoulder prosthesis system 100 should have the strength to withstand the loads, biocompatibility for implantation inside the body (e.g., by being non-toxic), not cause adverse reactions in the receiving patient (e.g., corroding), and provide adequate wear characteristics for the bearing surfaces. In some cases, regulatory agencies, such as the U.S. Food & Drug Administration, have specified the material options for the components of a typical reverse total shoulder prosthesis. For example, in some configurations, the socket 110 and the stem 112 can be configured as a monolithic piece, or two separate pieces that can be coupled together. In some cases, the cup 106 can be formed out of a polymer (e.g., polyethylene, or more specifically, ultra-high molecular weight polyethylene ("UHMWPE")). In some configurations, the glenosphere 104 can be formed from a metal, such as a CoCrMo alloy, titanium alloy, or stainless steel, while the baseplate 102 (and fasteners, as appropriate) can also be formed from a metal (e.g., a titanium alloy, or stainless steel alloy). In some cases, some surfaces of the baseplate 102 can have surface modifications (e.g., etching).

Figures 2A, 2B:
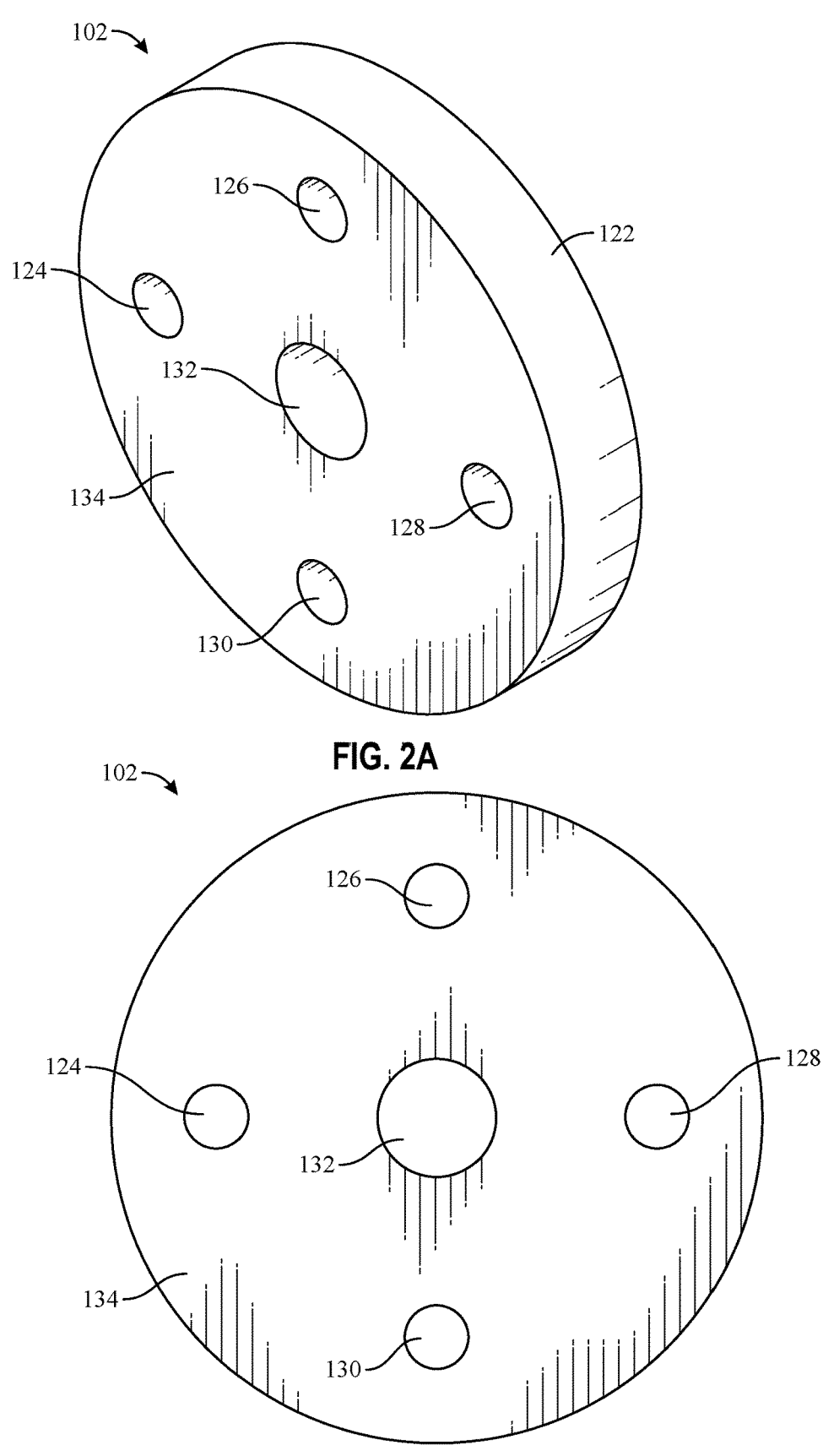
FIG. 2A shows a front isometric view of a baseplate of the reverse shoulder prosthesis system of FIG. 1.
FIG. 2B shows a front view of the baseplate of FIG. 2A.

FIG. 2A shows a front isometric view of the baseplate 102, while FIG. 2B shows a front view of the baseplate 102. As shown, the shape of the baseplate 102 is circular and defined by a peripheral surface 122; however, in alternative configurations, the baseplate 102 can be shaped differently (e.g., square, octagonal, etc.). The baseplate 102 includes holes 124, 126, 128, 130, 132 that each extend entirely through the thickness of the baseplate 102 (e.g., from a coupling surface 134 to an opposite mounting surface). Each hole 124, 126, 128, 130, 132 is configured to receive a fastener (e.g., a fixation screw) so that the baseplate 102 can be secured to the bone of the patient. In some cases, the peripheral surface that defines each hole can include threading that can engage with a corresponding fastener. As shown, the holes 124, 126, 128, 130 are all substantially (e.g., deviating by less than 20%) identical in size, and the hole 132 can be larger than the holes 124, 126, 128, 130 (e.g., to receive a larger fastener). In some cases, the holes 124, 126, 128, 130, rather than extending perpendicularly relative to the surface 134 of the baseplate 102, can extend through the baseplate 102 at an angle relative to the surface 134 other than 90 degrees.

Figure 3A:
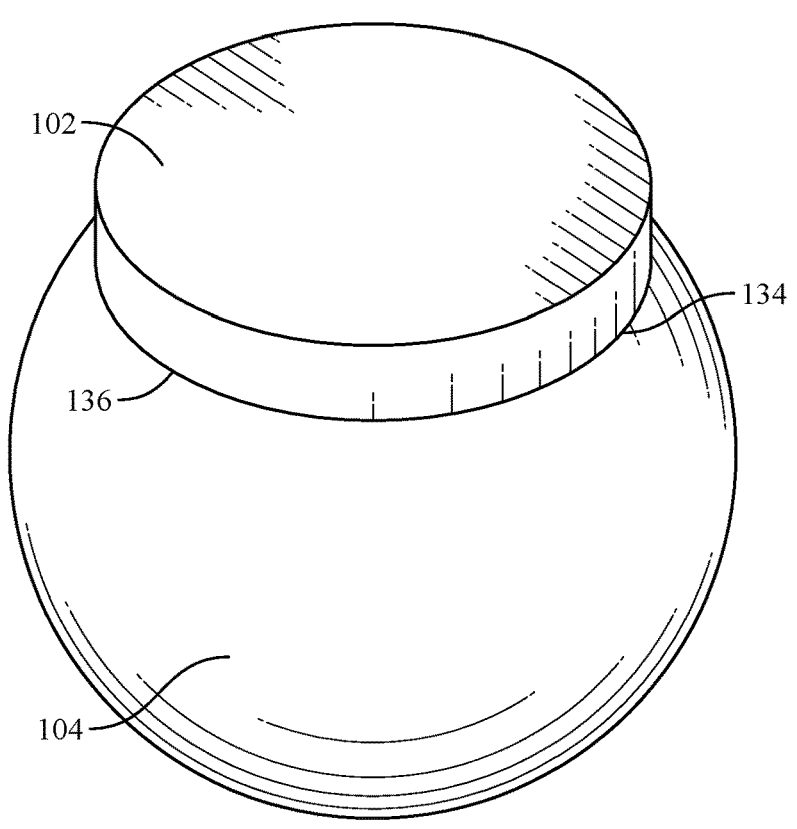
FIG. 3A shows an isometric view of an assembly including the baseplate coupled to a glenosphere.
Figure 3B:
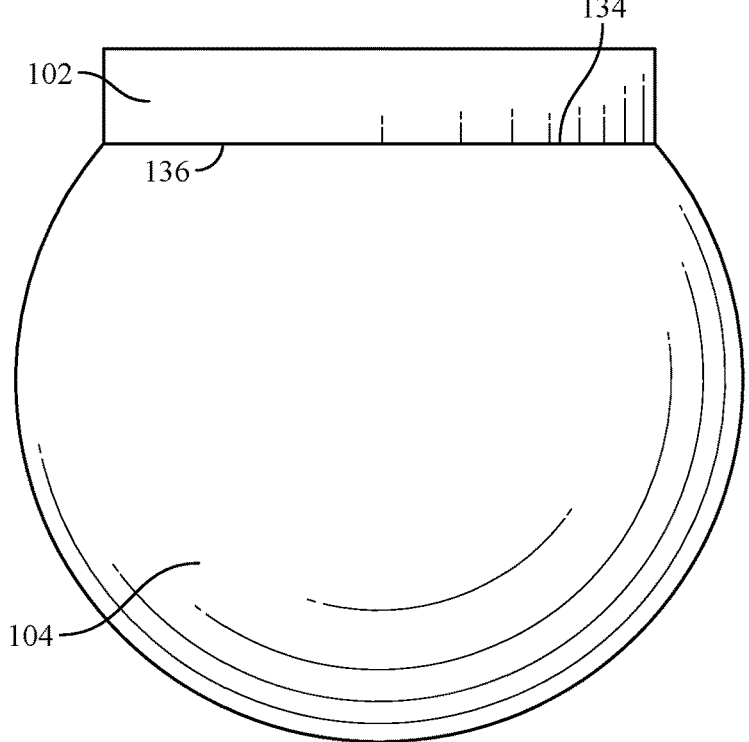
FIG. 3B shows a front view of the assembly of FIG. 3A.

FIG. 3A shows an isometric view of an assembly including the baseplate 102 coupled to the glenosphere 104, and FIG. 3B shows a front view of the assembly of FIG. 3A. As shown in FIGS. 3A and 3B, the holes of the baseplate 102 have been removed for visual clarity. In this configuration, a flat surface 136 of the glenosphere 104 is coupled to the coupling surface 134 of the baseplate 102 (e.g., with cement) so that the baseplate 102 is exteriorly positioned relative to the glenosphere 104.

In some embodiments, the glenosphere 104 can define a glenosphere center of rotation offset, which can be the height of the truncated section of the sphere that comprises the glenosphere 104. In other words, the glenosphere center of rotation offset can be defined between an end surface of the truncated end of the glenosphere 104 (e.g., the flat surface 136) and the equator of the glenosphere 104. In some cases, the glenoid center of rotation can be defined as the thickness of the baseplate 102. In some embodiments, the center of rotation offset of the glenosphere 104 can be defined as the sum of the glenosphere center of rotation offset and the glenoid center of rotation offset (e.g., the thickness of the baseplate 102).

In some embodiments, a radius of the glenosphere 104 can be in a range between 16 mm and 18 mm. In more specific cases, the radius of the glenosphere 104 can be less than 16 mm, or substantially less than 16 mm (e.g., deviating by 20%).

Figure 4A:
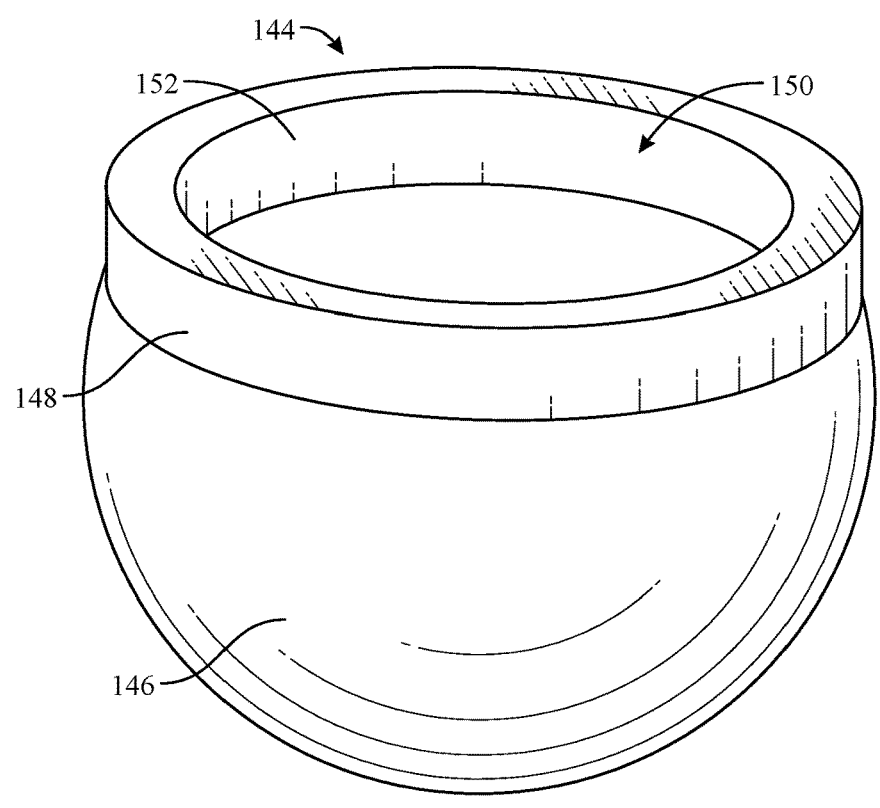
FIG. 4A shows an isometric view of another glenosphere.
Figure 4B:
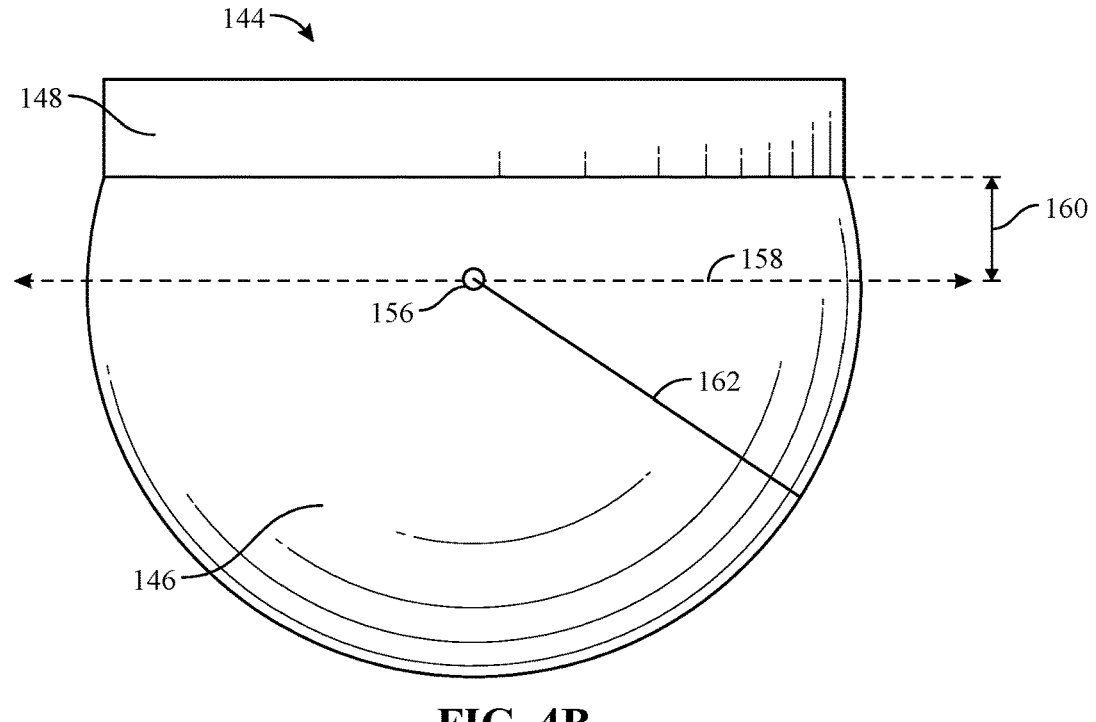
FIG. 4B shows a side view of the glenosphere of FIG. 4A.

FIG. 4A shows an isometric view of another glenosphere 144, and FIG. 4B shows a side view of the glenosphere 144. The glenosphere 144 may be a different configuration than a glenosphere 104 described above with respect to FIGS. 1-3B, but can be implemented with the system 100. In other words, the glenosphere 144 can replace the glenosphere 104 in the system 100 of FIG. 1. Similarly to the glenosphere 104, the glenosphere 144 also has a spherical portion 146, but also has a stem 148 extending from the spherical portion 146, which is cylindrical in shape. As shown, the stem 148 is integrally formed with the spherical portion 146, however, in alternative configurations the stem 148 can be coupled to the spherical portion 146. The glenosphere 144 also includes a bore 150 directed through one end of the glenosphere 144, opposite the end of the spherical portion 146. In particular, the bore 150 can be defined by a peripheral surface 152, extending through the entirety of the stem 148, and in some cases, past the stem 148 and partially into the spherical portion 146. In some embodiments, the bore 150 extends only partially through the stem 148. As shown, the bore 150 is cylindrical in shape, however, in other configurations, the bore 150 can have other shapes. The diameter of the bore 150 can be the same (or substantially similar) as the diameter of the baseplate 102 so that, when assembled, the baseplate 102 nests entirely within the bore 150 of the glenosphere 144. Thus, the diameter (or perimeter) of the stem 148 of the glenosphere 144 can be larger than the diameter (or perimeter) of the baseplate 102.

In some embodiments, the peripheral surface 152 that defines the bore 150 can contact the peripheral surface 122 of the baseplate 102 when the system 100 is assembled. In some configurations, the peripheral surface 152 of the glenosphere 144 can include threads and the peripheral surface 122 of the baseplate 102 can include threads so that the peripheral surface 152 can threadingly engage the peripheral surface 122 of the baseplate 102 to secure the glenosphere 144 to the baseplate 102. As shown in FIG. 4B, the spherical portion 146 defines a geometric center 156 that is located at the equator 158 of the spherical portion 146. The perpendicular distance 160, also known as the glenosphere center of rotation offset, as illustrated in FIG. 4B between the equator 158 (or the geometric center 156) of the spherical portion and an end of the spherical portion 146 connected to the stem 148 can be a percentage of the radius 162. In some embodiments, this percentage can in a range that is between a value close to 0% (e.g., 0% exclusive, or within a few percentages of 0%), corresponding to a glenosphere center of rotation offset 160 of slightly larger than 0 mm (e.g., 0 mm exclusive), and a value close to 100% (e.g., 100% exclusive, or within a few percentages of 100%). In some embodiments, this percentage can be in a range between 20% and 70%. In some specific cases, such as when the radius 162 is 16 mm, the glenosphere center of rotation offset 160 can be greater than and close to 4 mm (e.g., 4 mm exclusive, or a few percentages of and above 4 mm). In other specific cases, such as when the radius 162 is 18 mm, the glenosphere center of rotation offset 160 can be lower than and close to 10 mm (e.g., 10 mm exclusive, or a few percentages of and below 10 mm).

Figures 5A, 5B, 5C:
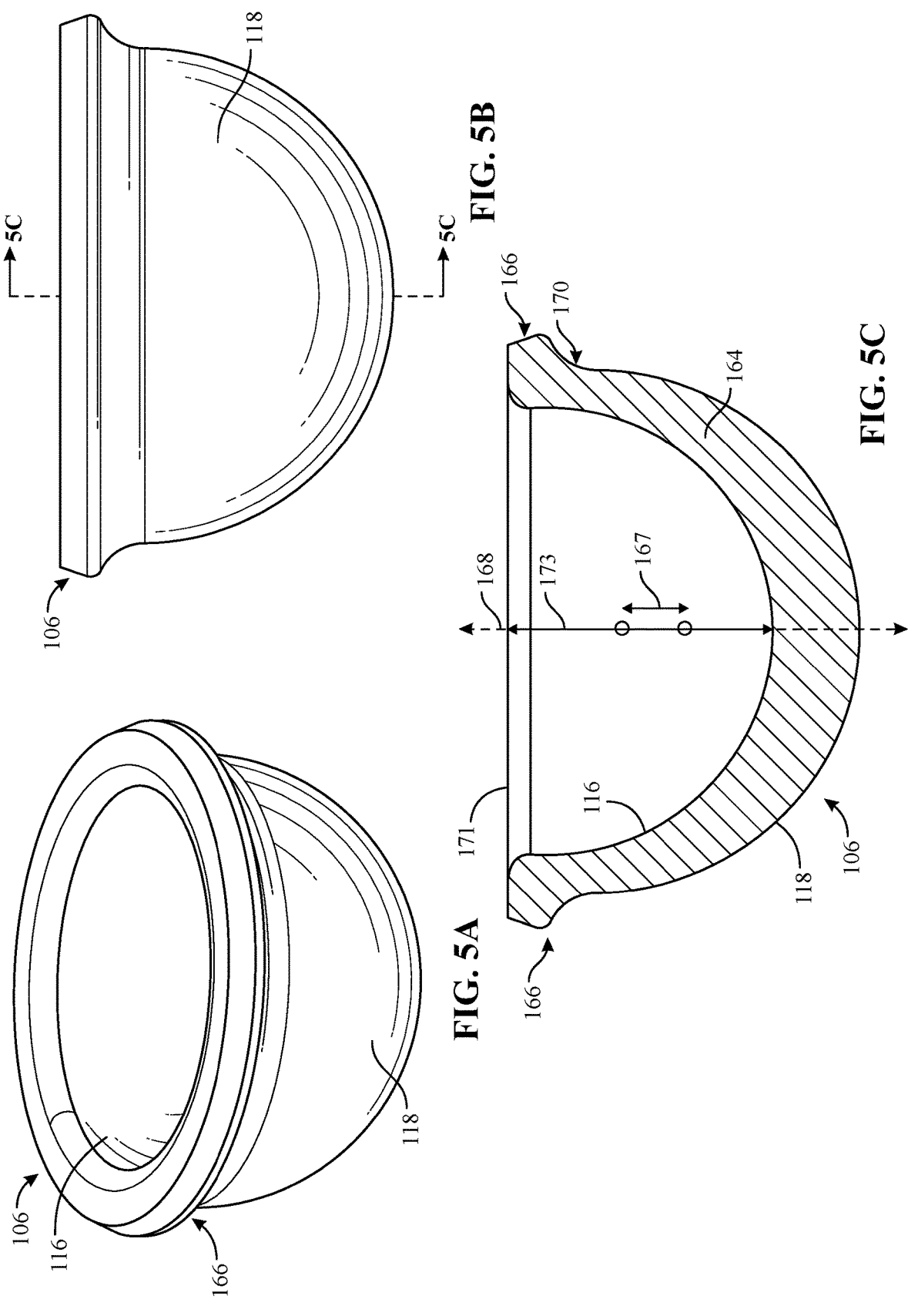
FIG. 5A shows a front isometric view of a cup of the reverse shoulder prosthesis system of FIG. 1.
FIG. 5B shows a front view of the cup of FIG. 5A.
FIG. 5C shows a cross-sectional view of the cup taken along line 5C-5C of FIG. 5B.

FIG. 5A shows a front isometric view of the cup 106, FIG. 5B shows a front view of the cup 106, and FIG. 5C shows a cross-sectional view of the cup taken along line 5C-5C of FIG. 5B. As described above, the cup 106 has opposing surfaces 116, 118 which can collectively define a thickness 164 of the cup 106. Because the surfaces 116, 118 have different radii of curvature, the thickness of the cup 106 varies from one side of the cup 106 to another (e.g., with reference to the orientation shown in FIG. 5C, the thickness is generally non-uniform increasing from the upper annular portion toward the lower base of the cup 106). In other words, the surface 116 has a first radius of curvature that corresponds to the radius of curvature of the glenosphere 104, while the surface 118 has a second radius of curvature that corresponds to the radius of curvature of the socket 110. In one embodiment, the opposing surfaces 116, 118 of the cup 106 are described as generally non-concentric, such that the thickness of the cup 106 defined at points between the opposing surfaces 116, 118 varies based on the offset between the opposing surfaces 116, 118 at that point. In some embodiments, and as illustrated, the first radius of curvature of the surface 116 is smaller than the second radius of curvature of the surface 118. In some configurations, the cup 106 can be snap-fitted on the glenosphere 104 (e.g., the dimensions of the surface 116 of the cup 106 and the surface 114 of the glenosphere 104 enable a snap-fitted engagement between these components), while the socket 110 may not be snap-fitted with the surface 118 of the cup 106. In some embodiments, the bearing surface between the surface 116 of the cup 106 and the glenosphere 104 can be semi-constrained, while the bearing surface between the surface 118 of the cup 106 and the surface 120 of the socket 110 can be non-constrained. Thus, the bearing interface between the surface 118 of the cup 106 and the surface 120 of the socket 110 can slide more easily than the bearing surface between the surface 116 of the cup 106 and the glenosphere 104.

In some embodiments, as shown in FIGS. 5A-5C, the cup 106 can include a flange 166 that extends circumferentially around a peripheral edge of the cup 106, and that extends radially away from a central axis 168 of the cup 106. In some cases, and as illustrated, the flange 166 extends circumferentially around the entire axis 168. In other cases, the flange 166 can extend partially around the entire axis 168, in a discontinuous manner around the axis 168 (e.g., the flange 166 having one or more gaps at points around the axis 168). In some embodiments, the flange 166 can define a concave exterior surface 170 that also extends circumferentially around the cup 106 (e.g., around the entire axis 168).

In some embodiments, the cup 106 can define a cup center offset 167 (or, in other words, shift), which can be the offset between the geometric centers of rotation of the inner surface 116 and the outer surface 118 of the cup 106 (e.g., because the surface 116, 118 are non-concentric). In some embodiments, the cup 106 can define a cup depth of coverage 173, which can be the distance between an entrance plane 171 of the cup 106 and the center of the inner surface 116.

Figures 6A, 6B, 6C:
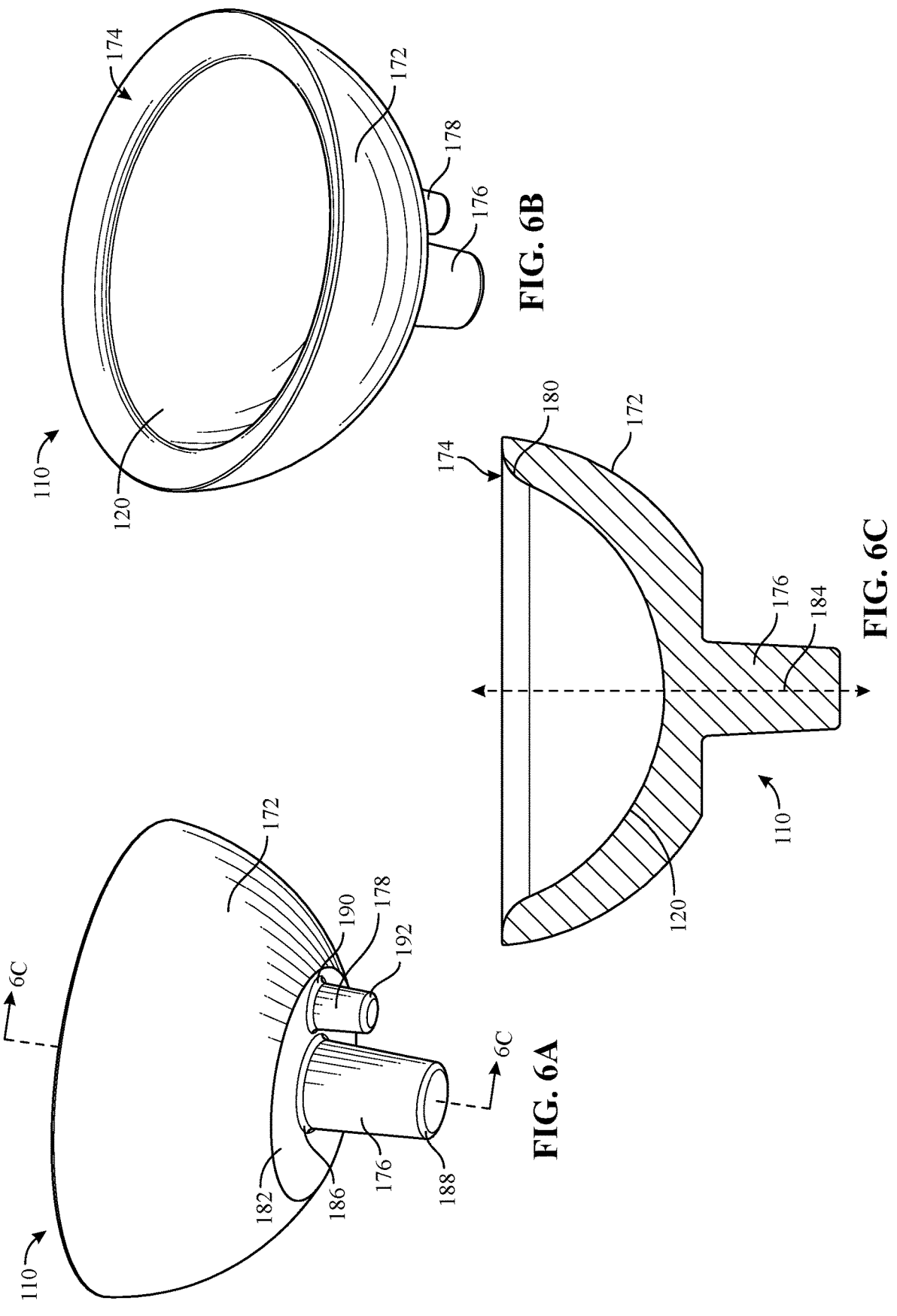
FIG. 6A shows a front isometric view of a socket of the reverse shoulder prosthesis system of FIG. 1.
FIG. 6B shows another isometric view of the socket of FIG. 6A.
FIG. 6C shows a cross-sectional view of the socket taken along line 6C-6C of FIG. 6A.

FIG. 6A shows a front isometric view of the socket 110, FIG. 6B shows another isometric view of the socket 110, and FIG. 6C shows a cross-sectional view of the socket 110 taken along line 6C-6C of FIG. 6A. Along with the surface 120 that is an interior concave surface, the socket 110 can also include an exterior convex surface 172, a lip 174 that extends circumferentially around the entire socket 110, and protrusions 176, 178. The lip 174 can have an arcuate convex surface 180 that also extends circumferentially around the entire socket 110, and which can be flush with the surface 120 of the socket 110. As shown, the protrusion 176 extends downwardly from a flat surface 182 that is located on an opposing end of the socket 110 away from the lip 174, along a central axis 184 of the socket 110 that bisects opposing sides of the socket 110. The protrusion 178 also extends downwardly from the flat surface 182 and is positioned laterally of the protrusion 176. Although the protrusions 176, 178 are illustrated as having a frustoconical shape, in other configurations, the protrusions 176, 178 can have other shapes. Additionally, although the protrusion 176 is illustrated as being longer and having a larger diameter than the protrusion 176, in other configurations, the protrusions 176, 178 can have different diameters and lengths.

In some embodiments, the protrusions 176, 178 have tapered surfaces. For example, as illustrated, the protrusion 176 has tapered surfaces 186, 188, while the protrusion 178 has tapered surfaces 190, 192. In particular, the tapered surface 186 is situated at an interface between an end of the protrusion 176 and the flat surface 182, and the tapered surface 188 is situated at a free end of the protrusion 176. Similarly, the tapered surface 190 is situated at an interface between an end of the protrusion 178 and the flat surface 182, and the tapered surface 192 is situated at a free end of the protrusion 178. The tapered surfaces 186, 188, 190, 192 can provide an interface that allows the protrusions 176, 178 to be coupled to the humeral stem 112 (or a different humeral stem, such as an existing humeral stem of a total shoulder replacement system that has failed). In some cases, the tapered surfaces 186, 188, 190, 192 can be Morse tapers. In some embodiments, the tapered surfaces 186, 188, 190, 192 can be tapered at the same angle, or in other cases, can each be tapered at different angles.

Figures 7A, 7B:
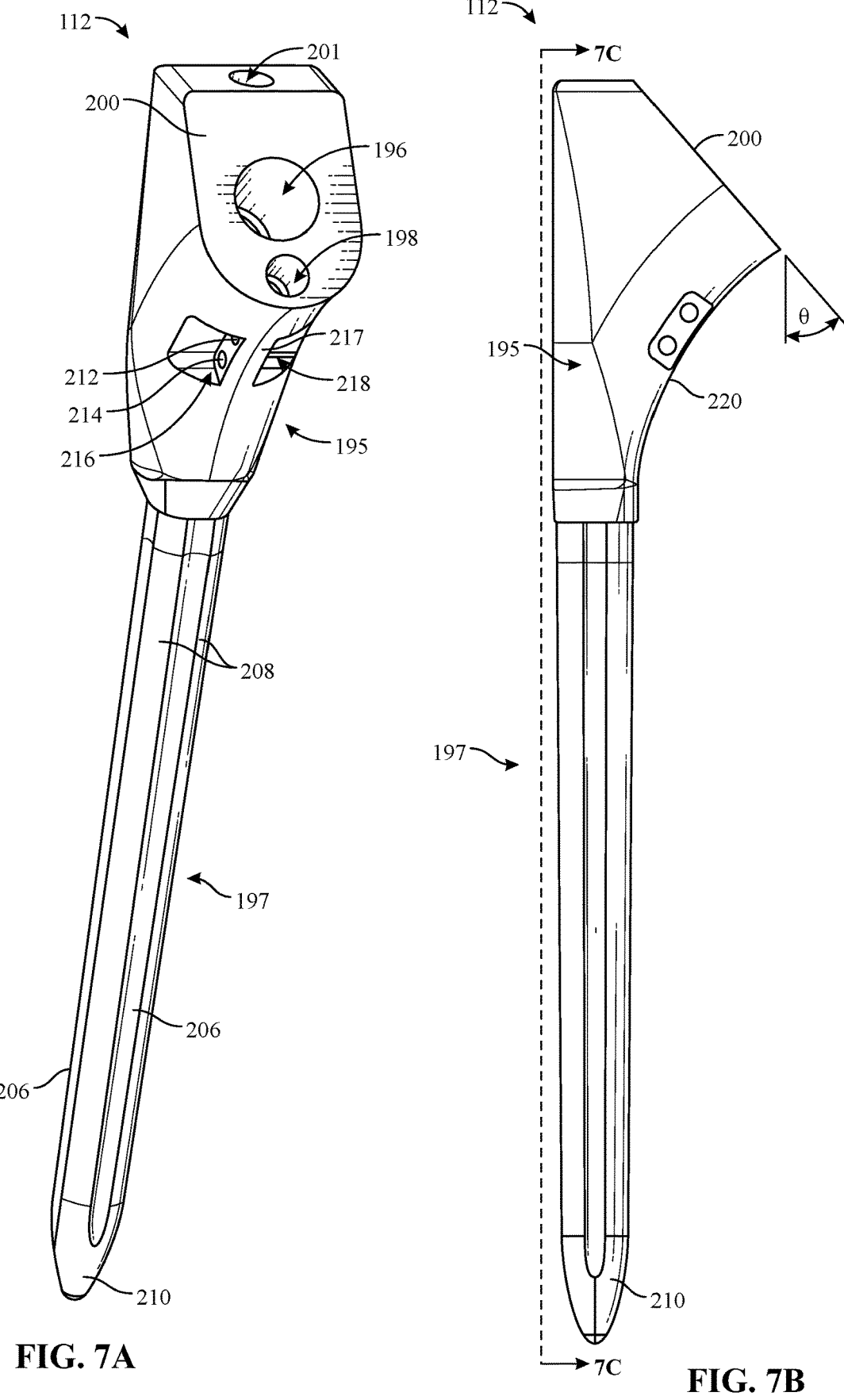
FIG. 7A shows an isometric view of a stem of the reverse shoulder prosthesis system of FIG. 1.
FIG. 7B shows a side view of the stem of FIG. 7A.
Figure 7C:
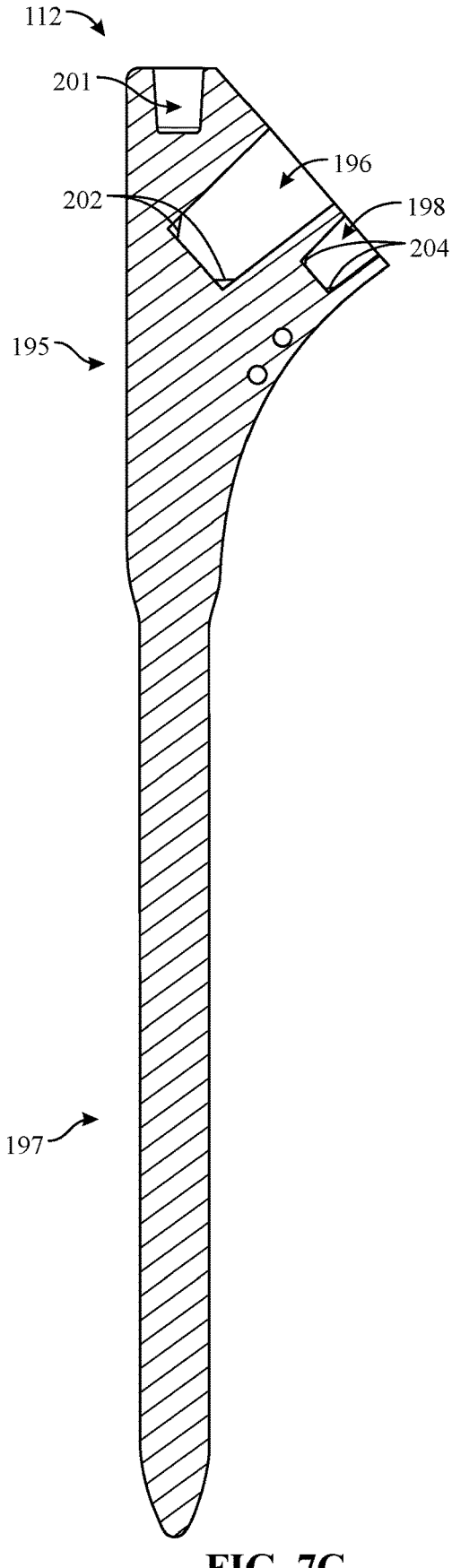
FIG. 7C shows a cross-sectional view of the stem taken along line 7C-7C of FIG. 7B.

FIGS. 7A and 7B each show different views of the stem 112, while FIG. 7C shows a cross-sectional view of the stem 112 taken along line 7C-7C of FIG. 7B. The stem 112 can include a neck 195, an arm 197 coupled to and extending from the neck 195, and bores 196, 198. The neck 195 can have an end surface 200 that is angled relative to a length of the arm 197 that extends from the neck 195 in a straight manner (e.g., the surface 200 is flat and forms an angle with the length of the arm 197 indicated in FIG. 7B as the angle θ). In some embodiments, the end surface 200 contacts the flat surface 182 of the socket 110 when the socket 110 is coupled to the stem 112. In some cases, a smaller humeral neck-shaft angle (e.g., angle θ when the socket 110 is coupled to the stem 112) contributes to a reduction in adduction deficit. Each of the bores 196, 198 are directed through and extend past the end surface 200 of the neck 195, and correspond respectively to the shape of the protrusions 176, 178 of the socket 110. For example, the bores 196, 198 are illustrated as also being frustoconical to match the protrusions 176, 178, however, the bores 196, 198 can be shaped differently if the protrusions 176, 178 are shaped differently.

As shown in FIG. 7C, an end of the bore 196 (opposite its open end) has a tapered surface 202 that extends circumferentially around the entire bore 196, and an end of the bore 198 (opposite its open end) has a tapered surface 204 that extends circumferentially around the entire bore 196. When the socket 110 is coupled to the humeral stem 112, the protrusion 176 is inserted into the bore 196 and the tapered surface 188 of the protrusion 176 engages with the tapered surface 202 of the bore 196 to secure the protrusion 176 within the bore 196. Similarly, when the socket 110 is coupled to the humeral stem 112, the protrusion 178 is inserted into the bore 198 and the tapered surface 192 of the protrusion 178 engages with the tapered surface 204 of the bore 198 to secure the protrusion 178 within the bore 198. Although not shown, opposing ends of the bores 196, 198 can also have tapered surfaces that each engage with the respective tapered surfaces 186, 190 of the corresponding protrusions 176, 178.

In some embodiments, as shown in FIG. 7A, the arm 197 of the stem 112 can have slots 206, each of which can be situated between tapered surfaces 208 of the arm 195 (e.g., the tapered surface 208 being tapered along the length of the arm 195 until reaching a tip 210 of the arm 195). The arm 197 is configured to be inserted into the humeral canal of the humerus of the patient to secure the stem 112. In some cases, the arm 197 can be dimensioned so that the arm 197 can be secured within the humeral canal without the use of adhesives (e.g., cement). For example, the surfaces of the arm 197 can engage the inner surfaces of the humeral canal to provide an interference fit. In other cases, the arm 197 can be cemented within the humeral canal with an adhesive.

In the illustrated embodiment, the stem 112 includes holes 212, 214 that are directed through a bridge 217 located between recesses 216, 218. The holes 212, 214 are illustrated as having the same size and shape (e.g., being circular), however the holes 212, 214 can take on other shapes. In some cases, the holes 212, 214 can each provide a mounting location for sutures. For example, sutures can be inserted through a respective hole 212, 214 inserted into a soft tissue structure, and tied at the respective hole 212, 214 to secure the soft tissue structure to the neck 195 of the stem 112. In some cases, the holes 212, 214 can be used for suturing the stem 112 with fractured humerus bone tissue, or when seen necessary for better positioning and stability of the stem 112. In some embodiments, a surface 220 extending between the surface 200 and the arm 197 can have a radius of curvature that can be adjusted based on desired design parameters of the stem 112.

In some embodiments, a bore 201 can be directed through a top surface of the neck 195 of stem 112. The bore 201 can be dimensioned and shaped to receive a tool (e.g., a post), which can provide an interface for directing the stem 112 into the patient's humerus, without potentially damaging the stem 112. For example, with the tool in mating engagement with the bore 201, a hammer (or other tool) can strike the tool to advance the stem 112 into the humerus of the patient without contacting the stem 112 with the hammer. In other embodiments, the bore 201 can be threaded to threadingly engage a tool that can be pulled to retreat the stem 112 out of the humerus (e.g., to more easily remove the implant, if the implant has failed).

In some embodiments, when the socket 110 is coupled to the stem 112, via the protrusions 176, 178 and corresponding bores 196, 198, the socket 110 (more specifically, the flat surface 182) is oriented and aligns with the angle θ (e.g., the angle that the surface 200 is oriented along). Additionally, in some cases, the protrusions 176, 178 (or other coupling components) of the socket 110 provide a modularity feature that allows the socket 110 to be fixed on stems of an anatomical total shoulder replacement (e.g., during the revision of a failed anatomical total shoulder replacement ("TSA")). In this way, if an anatomical total shoulder arthroplasty fails, the humeral stem from the failed total shoulder arthroplasty implant system can be utilized, and thus prevents the removal of this stem (e.g., which may decrease surgical complications, and quicken the surgical process of the reverse shoulder implant). In some embodiments, the socket 110 can be coupled to the stem 112 (or other stems, such as of a failed anatomical total shoulder arthroplasty implant system) in other ways, such as mechanical fasteners, adhesives (e.g., cement), etc.

In some embodiments, although not shown, the socket 110 can include a spacer (not shown) between the base of the socket 110 (e.g., between the flat surface 182 of the socket 110) and the end surface of the stem 112 (e.g., the surface 200 of the stem 112) to lengthen the humerus (e.g., when a smaller stem is preferred). This can provide a desirable surgical option during a reverse shoulder arthroplasty procedure. For example, the spacer can lengthen the humeral stem, and can add more lateralization for the socket 110 (e.g., when the socket 110 is coupled to the stem 112). In some embodiments, the spacer, when placed, can engage with the protrusions 176, 178 of the socket 110, and the spacer can engage with the bores 196, 198 of the stem 112 so that the socket 110 is indirectly engaged with the socket 112. In other cases, the protrusions 176, 178 can be made longer in length (than as illustrated) so that when a spacer is placed between the socket 110 and the stem 112, the protrusions 176, 178 are still able to properly engage the bores 198, 196 of the stem 112.

Figure 8:
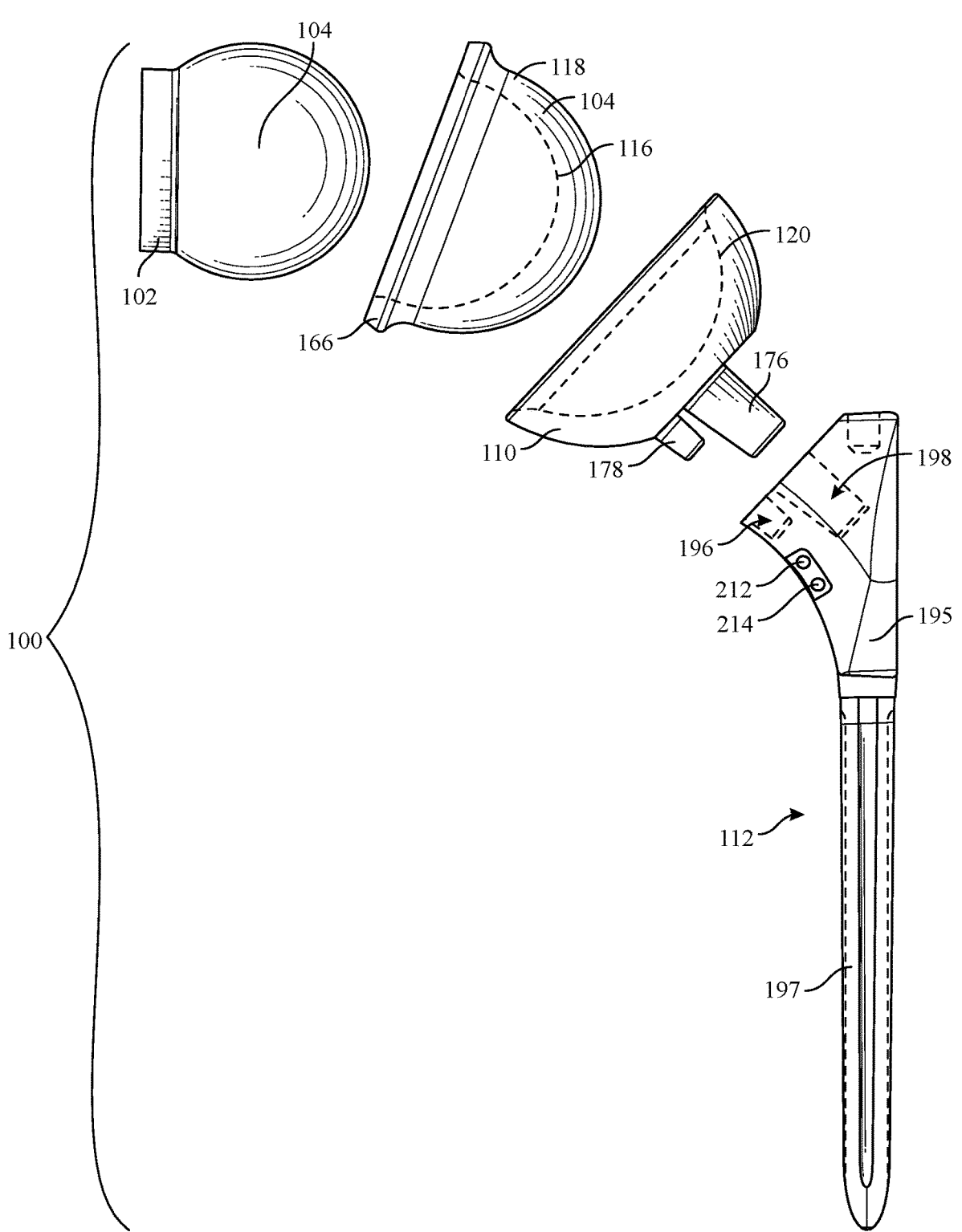
FIG. 8 shows an exploded view of the reverse shoulder prosthesis system of FIG. 1.

FIG. 8 shows an exploded view of the reverse shoulder prosthesis system 100, showing relative orientations of the glenosphere 104, the cup 106, the socket 110, and the stem 112. As shown, the baseplate 102 is coupled to the glenosphere 104, the cup 106 is engaged with the glenosphere 104 (e.g., snap-fitted), the socket 110 is coupled to the stem 112

(e.g., by seating the protrusion 176 within the bore 196 and the protrusion 178 within the bore 198, although other coupling configurations can be used such as fasteners), and the socket 110 is engaged with the cup 106.

Figure 9:
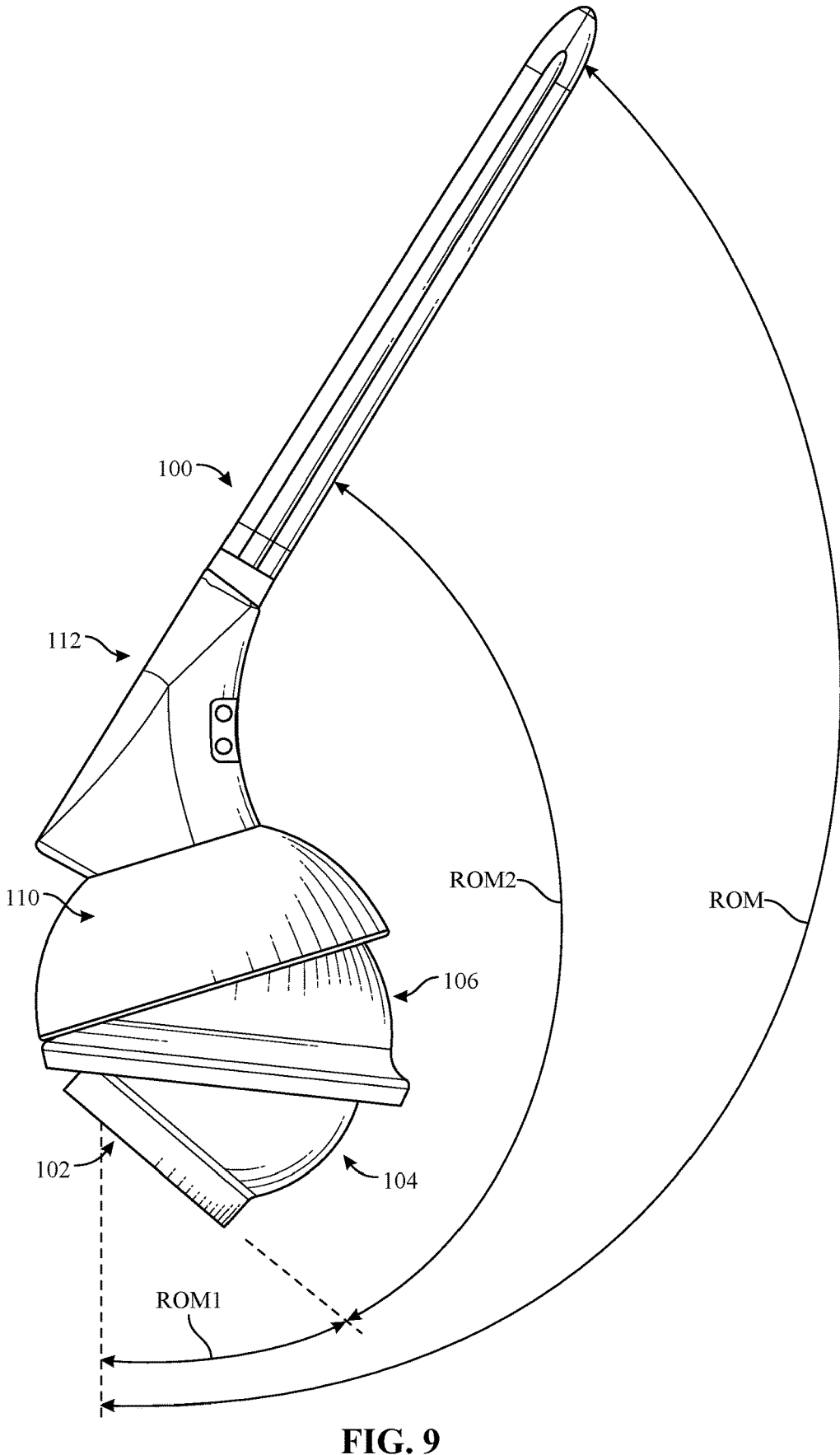
FIG. 9 shows the reverse shoulder prosthesis system of FIG. 8 assembled.

FIG. 9 shows the reverse shoulder prosthesis system 100 assembled, demonstrating how the components move to provide a larger range of motion (e.g., which can be defined from an end of the stem 112 relative to the baseplate 102) compared to conventional systems. For example, as shown in FIG. 9, the cup 106 articulates with both the glenosphere 104 and the socket 110 to provide an increased total range of motion of the system 100 (e.g., the scapulohumeral range of motion during abduction). In some embodiments, the cup 106 also provides a more dynamic adjustment of positions as compared to a typical reverse total shoulder implant. For example, in the typical reverse total shoulder implant, the entire mobility lies on the interface between the glenosphere and the humeral socket, as no cup is provided between the components. However, in the reverse should prosthesis system 100 described herein, the system 100 has two bearing surfaces, with one bearing surface between the glenosphere 104 and the cup 106, and with a second bearing surface between the cup 106 and the socket 110. Not only does this provide an increased range of motion, but this also provides a more dynamic adjustment of positions.

In some embodiments, a healthy shoulder abduction involves the motion of humerus and scapula approximately in the ratio of 2:1 (e.g., the glenohumeral versus the scapulothoracic). That is, for every two degrees of abduction by the humerus (indicated as ROM2 on FIG. 9), the scapula moves by one degree (indicated as ROM1 on FIG. 9). Typically, however, standard reverse shoulder designs have a ratio that is closer to 1:1, which leads to an average total abduction range of motion ("ROM") of 120 degrees (e.g., with 60 degrees from the scapula and another 60 degrees from the prosthesis). The reverse shoulder prosthesis system 100 with the cup 106 can provide an increased range of motion of the implant that exceeds these values to increase the total abduction range of motion (indicated as ROM on FIG. 9). For example, the range of motion of the system (e.g., ROM2) can be larger than 60 degrees, and the ratio of the range of motion of the humerus to the range of motion of the scapula can be larger than 1:1. In some cases, the ratio of the range of motion of the humerus to the range of motion of the scapula for the system can be substantially (e.g., ±20%) close to the 2:1 ratio.

Figure 10A:
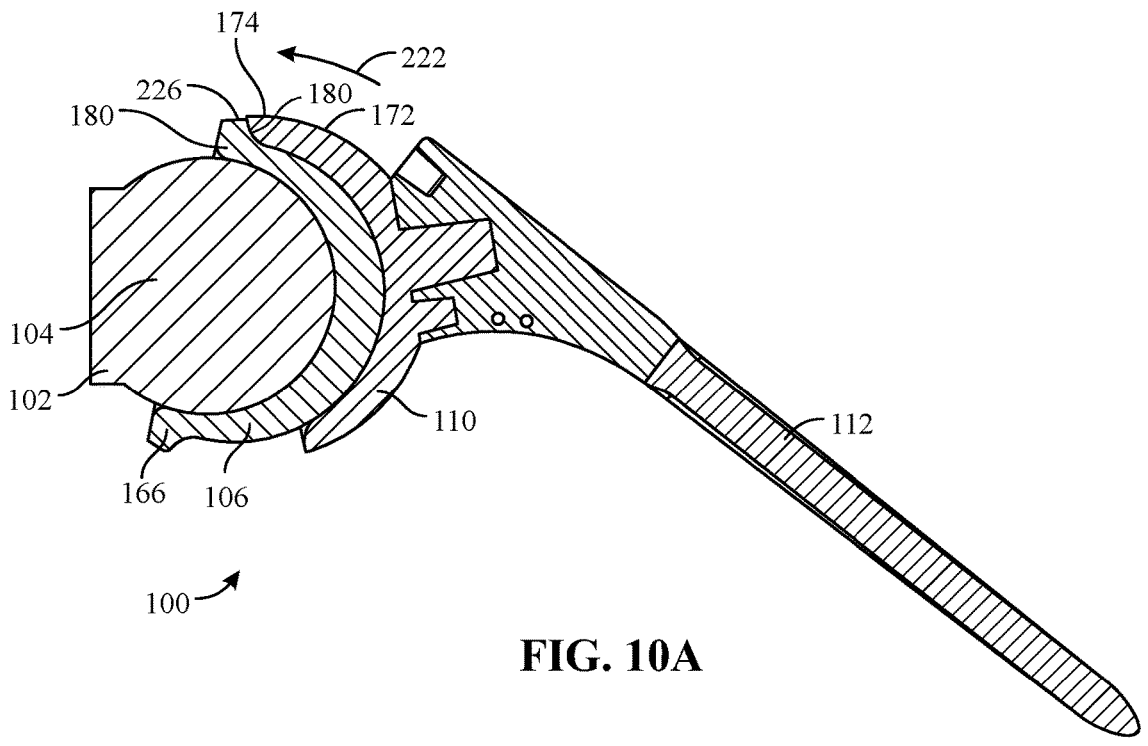
FIG. 10A shows a cross-sectional view of the reverse shoulder prosthesis system of FIG. 8 assembled and in one rotational position.
Figure 10B:
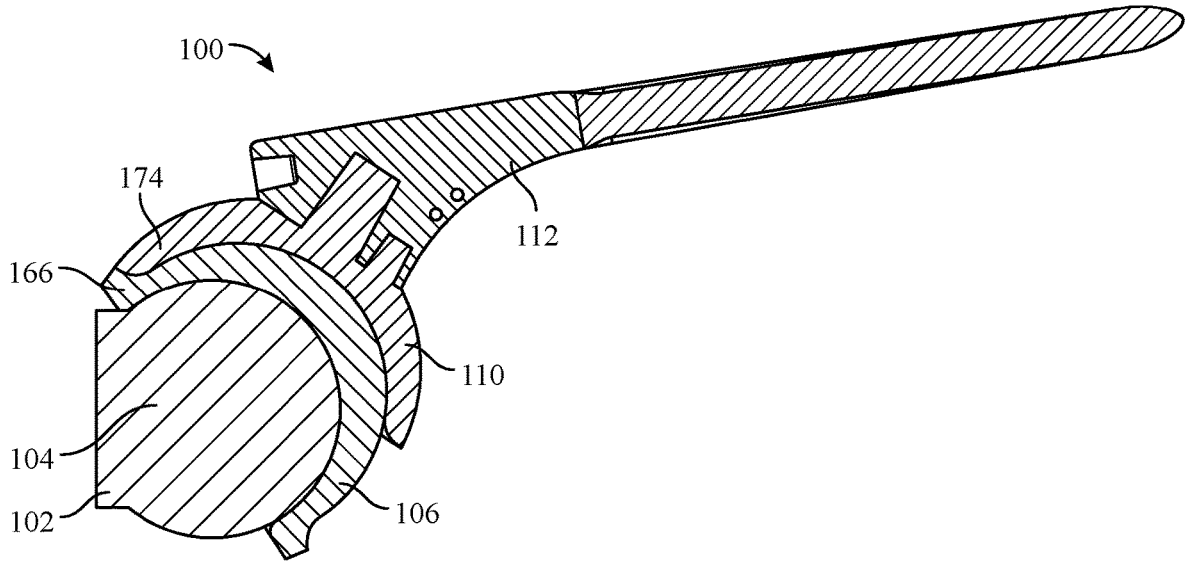
FIG. 10B shows another cross-sectional view of the reverse shoulder prosthesis system of FIG. 8 assembled and in a second rotational position, different from the first rotational position.

FIGS. 10A and 10B show cross-sectional views of the reverse shoulder prosthesis system 100 assembled and in two different rotational positions. In some embodiments, as the stem 112 is rotated in a first rotational direction 222 (e.g., by the patient moving their arm), the socket 110 moves relative to the cup 106 and the cup 106 moves relative to the glenosphere 104. In some embodiments, the movement between the socket 110 and the cup 106 occurs simultaneously with the movement between the cup 106 and the glenosphere 104, which can provide enhanced dynamics of the system 100 as opposed to previous reverse shoulder implants (e.g., the system 100 can absorb forces from movement of the stem 112 and translate them into movement of the cup 106 and the socket 110, providing less undesirable forces to the system 100). As the stem 112 is continually rotated in the first rotational direction 222, a gap between the lip 174 and the flange 166 decreases until the lip 174 of the socket 110 contacts and interfaces with the flange 166 of the cup 106. At this point, when the lip 174 of the socket 110 contacts the flange 166, further relative rotation between the socket 110 and the cup 106 is prevented. Rather, when the lip 174 contacts the flange 166 the socket 110 and the cup 106 rotate together (e.g., along the first rotational direction 222). FIG. 10A in particular shows when the lip 174 contacts the flange 166, and in particular shows the arcuate convex surface 180 of the lip 174 seating with the concave surface 170 of the flange 166. Additionally, and as illustrated, when the lip 174 contacts the flange 166, the exterior surface 172 of the socket 110 is flush and aligns with the exterior surface 226 of the flange 166.

FIG. 10B specifically shows the system 100 at a humeral range of motion limit for the stem 112, which in this case is a maximum abduction position of the stem 112. From the position of the system 100 illustrated in FIG. 10A, the stem 112 is further rotated in the first rotational direction 222 until the cup 106 contacts the baseplate 102. At this point, because the flange 166 of the cup 106 prevents further advancement of the socket 110 along the first rotational direction 222, the socket 110 is situated away from and does not contact either the baseplate 102 or the bone that the baseplate 102 is secured to (e.g., the scapula). Thus, the flange 166 of the cup 106 can prevent the socket 110 from contacting the bone that the baseplate 102 is connected to, or the baseplate 102 (e.g., minimizing or preventing impingement of the implant with surrounding bone tissue at a maximum range of motion, such as the maximum abduction position). In other words, the flange 166 of the cup 106 prevents the socket 110 from advancing past the flange 166 and thus prevents the socket 110 from advancing past the baseplate 102 and contacting the bone. While the dynamics of rotation described herein are made with simplified reference to the two-dimensional representation of, for instance, FIGS. 10A and 10B, the rotational dynamics provide for relative rotation in multiple directions (e.g., three degrees of freedom, including combinations of pitch, yaw, and roll).

In some embodiments, the flange 166 of the cup 106 can also prevent contact between the socket 110 and the glenosphere 104. For example, beginning at the position of the system 100 illustrated in FIG. 10A, if the flange 166 of the cup 106 were removed and the stem 112 rotated in the first rotational direction 222, only the socket 110 may rotate (or may rotate past the cup 106). In this case, the interior surface 120 of the socket 110 may contact the glenosphere 104, which can cause a degrading of these surfaces that can, over time, cause components of the system 100 to not move as intended. Additionally, because the socket 110 and the glenosphere 104 can both be formed of metal, the contact between the two can create undesirable metal on metal interface (e.g., which can potentially undesirably discharge metal ions that can be toxic or that can damage surrounding tissue or entire systems).

Figure 11A:
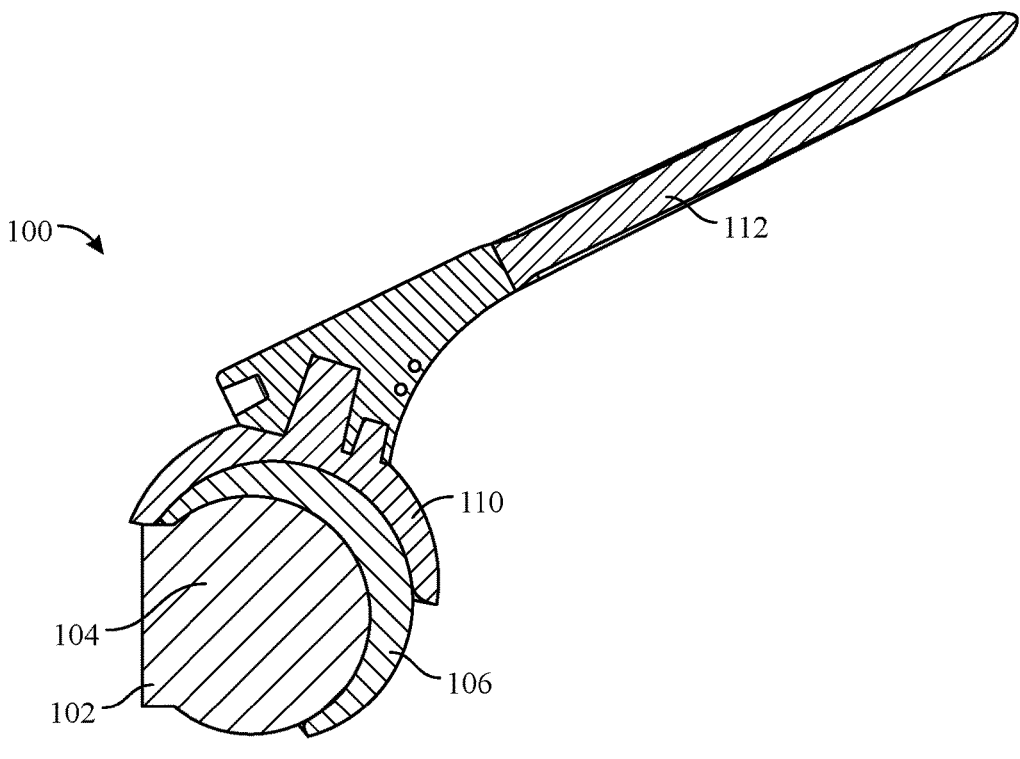
FIG. 11A shows a cross-sectional view of the system of FIG. 1 that has a cup without a flange, in a first rotational position.
Figure 11B:
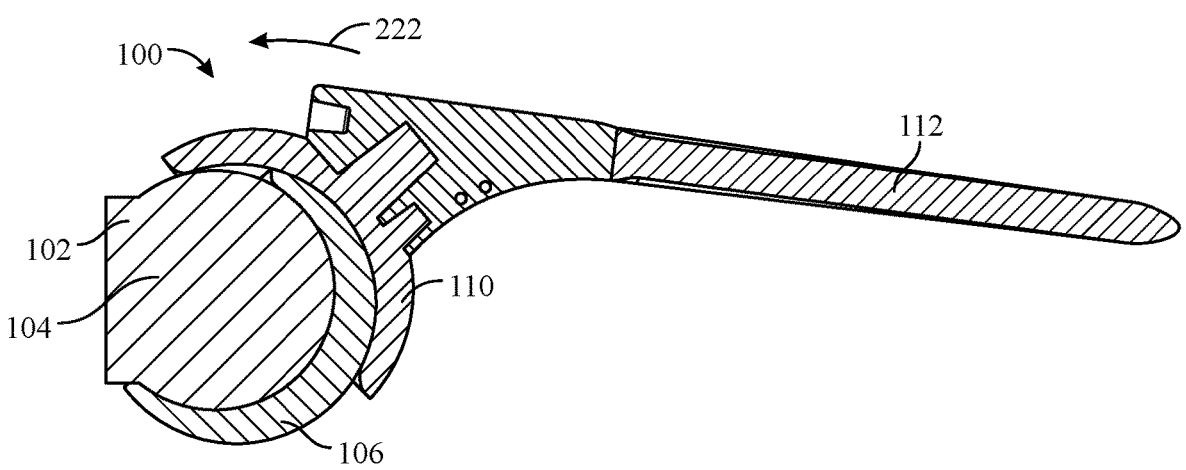
FIG. 11B shows a cross-sectional view of the system of FIG. 11A having the cup without the flange, in a second rotational position different from the first rotational position.

More specifically, FIGS. 11A and 11B show cross-sectional view of the system 100 that has a cup 106 without the flange 166. FIG. 11A shows the system in a maximum abduction position, where the socket 110 is in contact with the baseplate 102 and extends past the baseplate 102 to be in contact with the bone that the baseplate 102 is secured to (not shown). The flange 166 can mitigate this issue by ensuring that the socket 110 does not extend beyond the flange 166, thereby inhibiting impingement of the implant with the bone. Additionally, FIG. 11B shows the system rotated in the first rotational direction 222, with the socket 110 extending past a peripheral edge of the cup 106 to contact the glenosphere 104. The flange 166 can ensure that the cup 106 moves with the socket 110 as the socket 110 engages with the flange 166 during shoulder movement, preventing such contact between the socket 110 and the glenosphere 104.

Figures 12A, 12B:
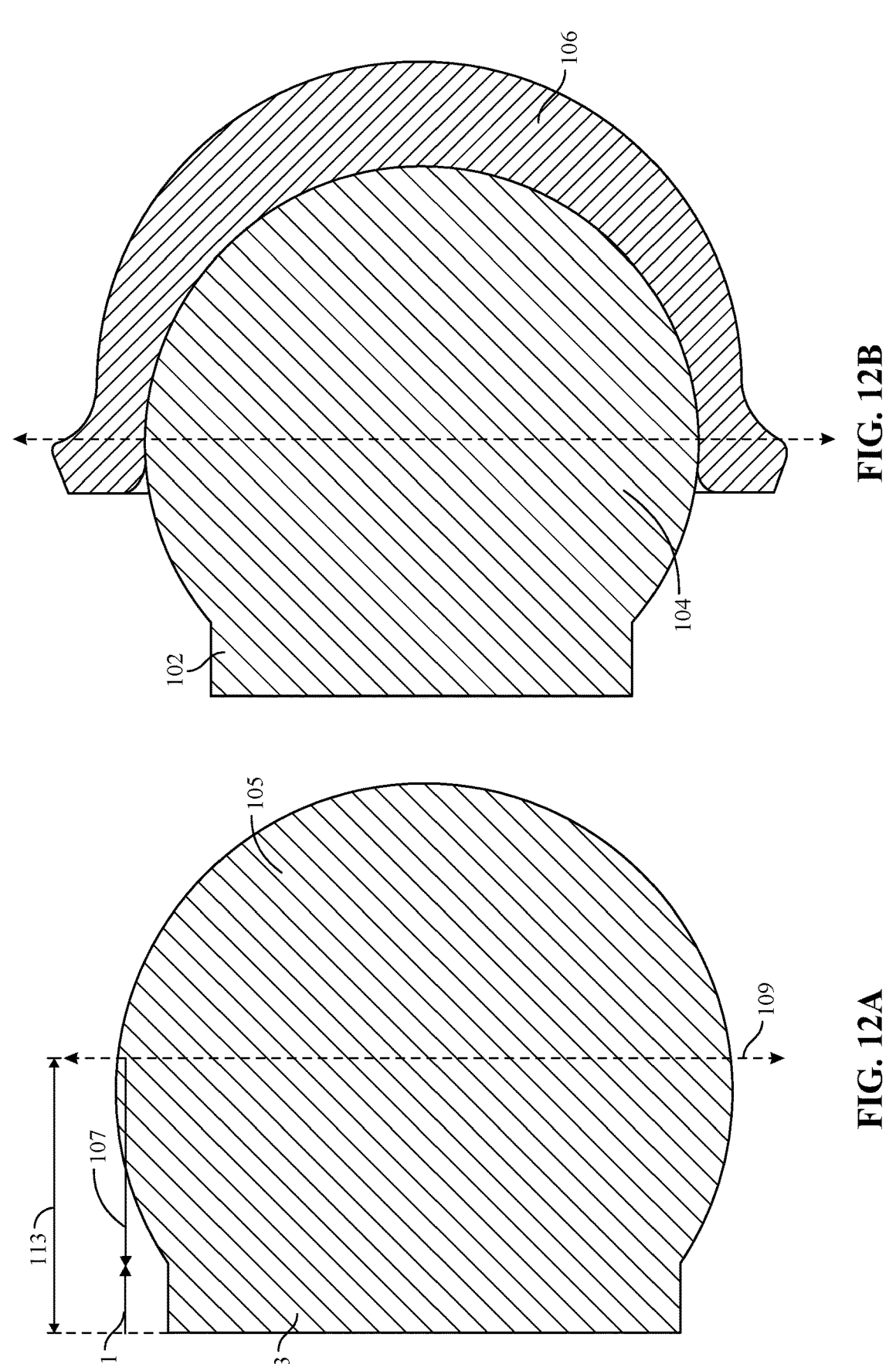
FIG. 12A shows a cross-sectional view of another glenosphere that has a baseplate coupled to an end of the glenosphere.
FIG. 12B also shows a cross-sectional view of the glenosphere interfaced with the cup, and coupled to the baseplate, all from the system of FIG. 1.

FIG. 12A shows a cross-sectional view of another glenosphere 105, including a baseplate 103 coupled to an end of the glenosphere 105. In some embodiments, the glenosphere 105 can define a glenosphere center of rotation 107 defined between an end surface of the truncated end of the glenosphere 105 and an equator 109 of the glenosphere 105, and the thickness of the baseplate 103 can define a center of rotation offset shift 111. The sum of the glenosphere center of rotation 107 and the center of rotation offset shift 111 can define the center of rotation offset 113 of the glenosphere 105. FIG. 12B also shows a cross-sectional view of the glenosphere 104 interfaced with the cup 106, and coupled to the baseplate 102. Similar to the glenosphere 105 of FIG. 12A, an end surface of the baseplate 102 and the equator of the glenosphere 104 can define a COR offset shift of the glenosphere 104 (e.g., the sum between the glenosphere center of rotation and the center of rotation offset shift provided by the baseplate 102). In some cases, commercially available reverse shoulder systems lateralize their designs by increasing the COR offset of the glenosphere (e.g., by increasing the size of the glenosphere). However, too much lateralization increases the stress on the baseplate-glenoid interface. The non-concentric design of the cup 106 (e.g., the inner surface 116 and the outer surface 118 being non-concentric) creates a lateral shift in the center of rotation for the socket 110 while minimizing (and preferably without adding) additional stress on the baseplate.

Additionally, as described above, increasing the center of rotation offset has advantages (e.g., increased range of motion) and disadvantages (e.g., increased stresses on the fixation location on the bone), which creates a trade-off. However, the inclusion of the cup 106 largely eliminates this trade-off. For example, both systems of FIGS. 12A and 12B have a similar range of motion. However, the first COR of the first system of FIG. 12A is larger than the second COR of the second system of FIG. 12B. Thus, with the inclusion of the cup 106 to provide a greater range of motion, the glenosphere 104 can be made smaller to minimize COR offset.

Figure 13:
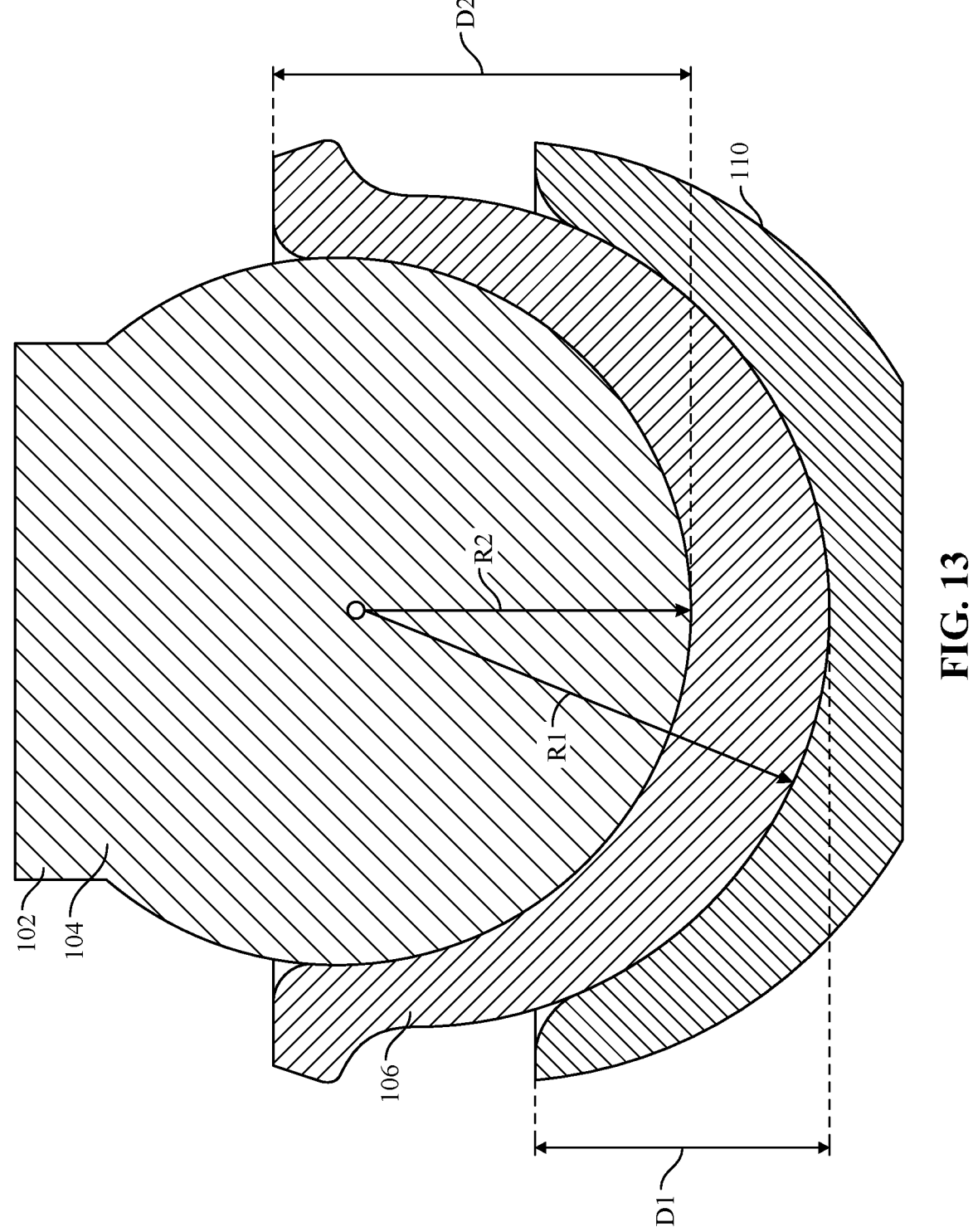
FIG. 13 shows a cross-sectional view of the baseplate, the glenosphere, the cup, and the socket, all from the system of FIG. 1.

FIG. 13 shows a cross-sectional view of the baseplate 102, the glenosphere 104, the cup 106, and the socket 110. As shown, the socket 110 has a depth (D1) defined between the minima of the surface 120 and a peripheral edge of the socket 110 (e.g., an end of the lip 174), while the cup 106 has a depth (d2) defined between the minima of the surface 116 and a peripheral edge of the cup 106 (e.g., an end of the flange 166). As also shown, the glenosphere 104 has a radius (R2), and the exterior surface 118 of the cup 106 also has a radius (R1). In some embodiments, the socket 110 can be designed to have the depth (D1) that is based on a specified D1/R1 ratio, which corresponds to the depth d1 over the radius of the cup contacting surface (i.e., R1). This creates a semi-constrained interface between the cup 106 and the socket 110. The d1/R1 ratio of the socket 110 can determine the degree of stability and the range of motion of the shoulder joint. In some cases, the D1/R1 ratio can be about (e.g., ±40 percent) or exactly equal to 0.45. In other cases, the D1/R1 ratio can be substantially 0.45. The glenosphere 104 can also be designed to have radius R2, and the cup 106 can have a depth (i.e., D2) that can both result in a specific D2/R2 ratio. In some embodiments, this D2/R2 ratio can create a constrained interface between the glenosphere 104 and the cup 106.

EXAMPLES

The following examples have been presented in order to further illustrate aspects of the disclosure, and are not meant to limit the scope of the disclosure in any way. The examples below are intended to be examples of the present disclosure and these (and other aspects of the disclosure) are not to be bounded by theory. For example, the specific dimensions of any particular implementation of the concepts described in connection with the example reverse shoulder prosthesis system 100 may be tailored to the anatomy of any particular patient.

In some embodiments, the specifications detailed herein cover a shoulder prosthesis for reverse shoulder arthroplasty. Some goals of the reverse shoulder implant described herein are to improve the functional outcome of currently available implants. For example, this system aims to increase the range of motion of the joint, mitigate the risk of joint dislocation by increasing stability, and reduce scapular bone impingement.

In some embodiments, a larger contact surface area for the socket is desirable for scapular impingement reduction and better external/internal rotation, while a smaller glenosphere is desirable to achieve a better fixation on the glenoid fossa during surgery. Commercially available glenospheres can either focus on improving fixation by having smaller sizes, or reducing scapular impingement by having larger glenospheres. The dual mobility cup liner described herein eliminates the tradeoff between impingement and fixation through its design by combining both benefits.

The outer surface of the dual mobility cup liner can have a diameter that matches the size of commercially available glenospheres. However, in some cases, due to the increased range of motion provided by the dual mobility cup, the glenosphere can even be made smaller in size. In this way, the smaller glenosphere can be attached to the glenoid fossa of the patient through its baseplate, while still maintaining a larger contact surface for the socket.

In some embodiments, the stability of the replaced joint can be increased by tensioning the deltoid muscle. While commercially available reverse shoulder implants can implement this by having an additional spacer component, the non-concentricity of the dual mobility cup liner inherently contributes to lengthening the humerus and thereby tensioning the deltoid.

In some embodiments, the system described herein can increase joint range of motion by adding to the overall COR offset through the non-concentricity of the dual cup, and can increase the arc of contact of a smaller glenosphere. Abduction impingement caused by larger glenospheres of commercially available implants can also be reduced (e.g., due to the use of smaller glenosphere for this design), which can provide an increase in the impingement free range of motion.

In some embodiments, complex relationships between the design parameters, biomechanics, surgical procedures, and the outcomes for a reverse shoulder prosthesis system are to be considered. While all the design parameters may not have equal weight of contribution to the outcomes, it is worth looking at the effects. Range of motion, adduction deficit, and stability are some of the outcomes to consider.

Figure 14:
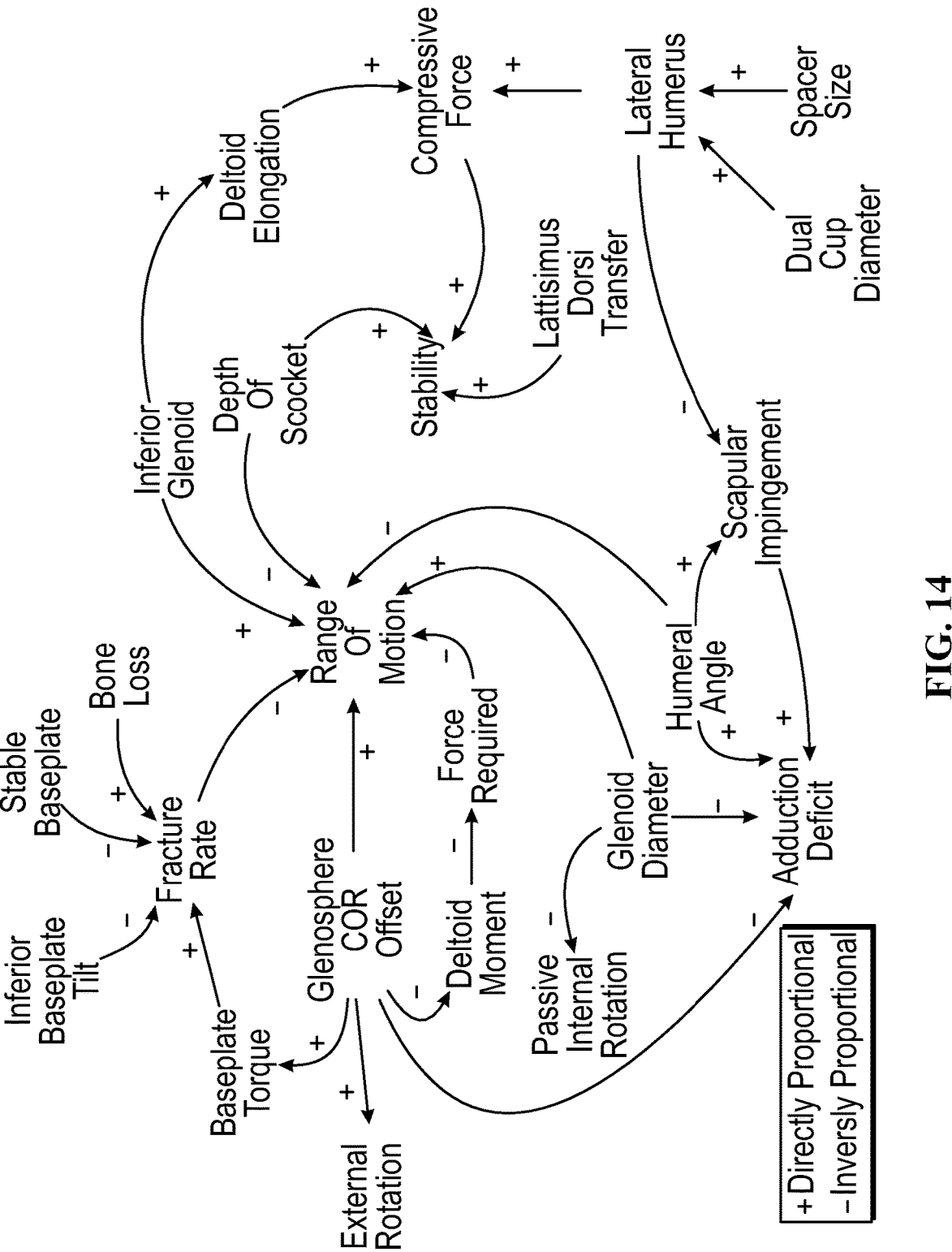
FIG. 14 shows a diagram of a causal loop for main parameters in a reverse shoulder prosthesis system.

FIG. 14 shows a diagram of a causal loop for main parameters in a reverse shoulder prosthesis system. In some cases, an increase in the lateralization of the glenoid system increases the range of motion of the implant and decreases the adduction deficit. This is usually achieved by increasing the COR offset of the glenosphere, which facilitates a larger arc of contact for the socket. The increase in COR offset also increases external rotation. However, this increase in the offset increases torque on the baseplate, which over time, increases the probability of fractures at the baseplate-glenoid bone interface. In some cases, this probability can be reduced by inferiorly tilting the baseplate during reverse shoulder arthroplasty procedure.

In some cases, an increase in the glenosphere diameter contributes to an increase in the arc of contact for the socket, thereby increasing the range of motion, and decreasing the adduction deficit. This case is applicable when the depth of the socket is constant. However, the increase in glenosphere diameter decreases the passive internal rotation and also makes it challenging for fixation during surgery.

In some cases, another factor governing the increase in impingement free range of motion and decrease in adduction deficit is the decrease in the humeral stem neck-shaft angle. It is also possible to achieve a decrease in the adduction deficit by lateralizing the humerus with the use of a spacer, thus reducing scapular impingement.

In some cases, lateralizing the humerus increases the compressive force of the deltoid muscle, which in turn increases the stability of the joint. The compressive force of the deltoid muscle can be increased by elongating the muscle through inferior glenosphere placement during the surgery. Some studies have shown that placing the glenoid system of the reverse shoulder implant inferiorly contributes to the increase in the range of motion. Increasing stability can also be accomplished by an increase in the d/R ratio, however, this will result in a reduction in the range of motion.

The dual mobility cup liner component, as described herein, increases the COR offset without changing the COR offset of the glenosphere, at least maintains the same arc of contact as that of commercial glenospheres while decreasing the size of the glenosphere, and lateralizes the humeral component and increases stability through deltoid tensioning.

The present disclosure has described one or more preferred embodiments, and it should be appreciated that many equivalents, alternatives, variations, and modifications, aside from those expressly stated, are possible and within the scope of the invention.

It is to be understood that the disclosure is not limited in its application to the details of construction and the arrangement of components set forth in the accompanying description or illustrated in the accompanying drawings. Given the benefits of this disclosure, one skilled in the art will appreciate that the disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, unless otherwise limited or defined, discussion of particular directions is provided by example only, with regard to particular embodiments or relevant illustrations. For example, discussion of "top," "front," or "back" features is generally intended as a description only of the orientation of such features relative to a reference frame of a particular example or illustration. Correspondingly, for example, a "top" feature may sometimes be disposed below a "bottom" feature (and so on), in some arrangements or embodiments. Further, references to particular rotational or other movements (e.g., counterclockwise rotation) is generally intended as a description only of movement relative to a reference frame of a particular example of illustration.

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as embodiments of the disclosure, of the utilized features and implemented capabilities of such device or system.

As used herein, unless otherwise defined or limited, ordinal numbers are used herein for convenience of reference based generally on the order in which particular components are presented for the relevant part of the disclosure. In this regard, for example, designations such as "first," "second," etc., generally indicate only the order in which the relevant component is introduced for discussion and generally do not indicate or require a particular spatial arrangement, functional or structural primacy or order.

As used herein, unless otherwise defined or limited, directional terms are used for convenience of reference for discussion of particular figures or examples. For example, references to downward (or other) directions or top (or other) positions may be used to discuss aspects of a particular example or figure, but do not necessarily require similar orientation or geometry in all installations or configurations.

This discussion is presented to enable a person skilled in the art to make and use embodiments of the disclosure. Given the benefit of this disclosure, various modifications to the illustrated examples will be readily apparent to those skilled in the art, and the generic principles herein can be applied to other examples and applications without departing from the principles disclosed herein. Thus, embodiments of the disclosure are not intended to be limited to embodiments shown, but are to be accorded the widest scope consistent with the principles and features disclosed herein and the claims below. The detailed description is to be read with reference to the figures, in which like elements in different figures have like reference numerals. The figures, which are not necessarily to scale, depict selected examples and are not intended to limit the scope of the disclosure. Skilled artisans will recognize the examples provided herein have many useful alternatives and fall within the scope of the disclosure.

Various features and advantages of the disclosure are set forth in the following claims.

What is claimed is:

1. A reverse shoulder prosthesis system, the system comprising:

a baseplate having a coupling surface and an opposite mounting surface with a peripheral surface connecting the coupling surface and the mounting surface to define a thickness of the baseplate therebetween;

a glenosphere coupled to the baseplate, the glenosphere having a truncated spherical portion with a flat surface coupled to the coupling surface of the baseplate, the truncated spherical portion having an equator and a geometric center defined at the equator and located along a central axis of the glenosphere that is axially distanced from the mounting surface of the baseplate to define a total offset of the glenosphere, the truncated spherical portion including an exterior convex surface defining a radius from the geometric center of the glenosphere, the equator being disposed in a first plane and the flat surface being disposed in a second plane parallel to the first plane with each of the equator and the flat surface being centered about the central axis of the glenosphere with a perpendicular distance between the first and second planes defining a glenosphere center of rotation offset;

a humeral socket having an interior concave surface extending circumferentially about a central axis of the humeral socket and a peripheral edge extending circumferentially about the central axis of the socket, the peripheral edge being axially spaced from an intersection of the central axis of the socket and the interior concave surface to define a depth (D1) of the humeral socket; and a cup positioned between the exterior convex surface of the glenosphere and the interior concave surface of the humeral socket, the cup being moveable relative to the glenosphere and to the humeral socket, the cup having a first cup surface and an opposing second cup surface defining a thickness of the cup therebetween, each of the first and second cup surfaces extending circumferentially about a central cup axis, the first cup surface having a first radius (R1) along the central cup axis and forming an exterior convex surface of the cup in bearing engagement with the interior concave surface of the humeral socket, the second cup surface having a second radius (R2) along the central cup axis and forming an interior concave surface of the cup in bearing contact engagement with the exterior convex surface of the glenosphere, wherein a ratio of the depth (D1) of the humeral socket to the first radius (R1) of the first cup surface (D1:R1) is 0.45+40 percent.

2. The system of claim 1, further comprising a humeral stem coupled to the humeral socket, the humeral stem having an end surface engaged with the humeral socket, and a tip with a neck extending axially between the end surface and the tip, wherein the cup articulates with respect to both the glenosphere and the humeral socket to define a total abduction range of motion of the system (ROM) between the tip and the baseplate that includes a ratio of humerus range of motion to scapula range of motion (ROM2:ROM1), wherein said ratio ROM2:ROM1 is 2:1±20 percent.

3. The system of claim 1, wherein the humeral socket is configured to be coupled to a humeral stem of a shoulder prosthesis system that has failed.

4. The system of claim 1, wherein the first radius (R1) is smaller than the second radius (R2).

5. The system of claim 1, wherein the flat surface of the truncated spherical portion of the glenosphere defines a diameter about the central axis of the glenosphere, the baseplate having a maximum width equal to the diameter of the truncated spherical portion, the baseplate being coupled to the truncated spherical portion such that the peripheral surface of the baseplate extends parallel to the central cup axis, wherein the cup has a flange that extends circumferentially around a peripheral edge of the cup, the flange extending radially away from a central axis of the cup, wherein at a maximum abduction position defining a humeral range of motion limit of the system, the peripheral edge of the cup contacts the peripheral surface of the baseplate and the flange situates the peripheral edge of the socket away from and out of contact with the baseplate.

6. The system of claim 5, wherein a gap is defined between a surface of the flange and an edge of the humeral socket, and wherein as the humeral socket rotates in a first rotational direction, the gap is minimized until the edge of the humeral socket contacts the surface of the flange.

7. The system of claim 6, wherein the cup is configured such that when the edge of the humeral socket contacts the surface of the flange, further rotation of the humeral socket in the first rotational direction causes the cup to rotate in the first rotational direction relative to the glenosphere.

8. The system of claim 5, wherein the flange includes an exterior concave surface that extends circumferentially around the cup, wherein the peripheral edge of the humeral socket defines an arcuate lip having an arcuate convex surface that extends circumferentially about the central axis of the humeral socket, and wherein at the maximum abduction position defining the humeral range of motion limit of the system, the arcuate convex surface of the arcuate lip is seated at the exterior concave surface of the flange to have an exterior surface of the humeral socket be flush and aligned with an exterior surface of the flange.

9. The system of claim 1, wherein the humeral socket is configured to rotate together with the cup, and is configured to rotate relative to the cup.

10. The system of claim 1, wherein the opposing first and second surfaces of the cup are non-concentric, wherein the thickness of the cup varies based on an offset between the opposing first and second cup surfaces, and an axial distance from the mounting surface of the baseplate and the truncated spherical portion define a center of rotation offset shift.

11. The system of claim 1, wherein the glenosphere includes a stem positioned at an end of the glenosphere, and a bore directed through the stem, and wherein the baseplate is sized to nest within the bore of the glenosphere.

12. The system of claim 11, wherein the stem is integrally formed with the glenosphere.

13. The system of claim 1, wherein the cup is snap-fitted onto the glenosphere.

14. The system of claim 1, wherein the flat surface of the truncated spherical portion of the glenosphere defines a diameter about the central axis of the glenosphere, the baseplate having a maximum width equal to the diameter of the truncated spherical portion, the baseplate being coupled to the truncated spherical portion such that the peripheral surface of the baseplate extends parallel to the central cup axis, wherein the second cup surface and the first cup surface form a peripheral edge of the cup therebetween that extends circumferentially about the central cup axis to define an entrance plane of the cup, and wherein at a maximum abduction position defining a humeral range of motion limit of the system, each of the peripheral edge of the cup and the peripheral edge of the humeral socket contacts the peripheral surface of the baseplate.

15. The system of claim 1, wherein the glenosphere center of rotation offset is between 20% and 70% from the geometric center of the glenosphere.

16. The system of claim 15, wherein the glenosphere center of rotation offset is 25% of the radius from the geometric center of the glenosphere.

17. The system of claim 15, wherein the glenosphere center of rotation offset is 55% of the radius from the geometric center of the glenosphere.

18. The system of claim 1, wherein the baseplate includes holes through the thickness of the baseplate to accommodate fasteners through the coupling surface and the mounting surface.

19. The system of claim 18, wherein the holes include a centrally located hole and a plurality of holes radially spaced from the centrally located hole.

20. The system of claim 18, wherein the holes extend through the thickness of the baseplate non-perpendicularly relative to the mounting surface.

21. The system of claim 1, wherein at a maximum abduction position defining a humeral range of motion limit of the system, the cup maintains contact with the glenosphere and the peripheral surface of the baseplate.

22. The system of claim 1, wherein the bearing contact engagement between the first cup surface and the interior concave surface of the from the geometric center socket enables more freedom of movement than that enabled by the bearing contact engagement between the second cup surface and the exterior convex surface of the glenosphere.

23. The system of claim 1, wherein the baseplate is fully exteriorly located relative to the glenosphere.

* * * * *